United States Patent
Takita et al.

(10) Patent No.: US 8,895,318 B2
(45) Date of Patent: Nov. 25, 2014

(54) AMMONIA COMPOUND CONCENTRATION MEASURING DEVICE AND AMMONIA COMPOUND CONCENTRATION MEASURING METHOD

(75) Inventors: Atsushi Takita, Tokyo (JP); Masazumi Tanoura, Tokyo (JP); Kenji Muta, Tokyo (JP); Shinichiro Asami, Tokyo (JP); Kageharu Moriyama, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 46 days.

(21) Appl. No.: 13/806,477

(22) PCT Filed: Sep. 28, 2010

(86) PCT No.: PCT/JP2010/066834
§ 371 (c)(1),
(2), (4) Date: Feb. 28, 2013

(87) PCT Pub. No.: WO2011/161839
PCT Pub. Date: Dec. 29, 2011

(65) Prior Publication Data
US 2013/0157377 A1    Jun. 20, 2013

(30) Foreign Application Priority Data
Jun. 24, 2010  (JP) ................. 2010-144300

(51) Int. Cl.
*G01N 21/59*    (2006.01)
*G01N 1/22*     (2006.01)
*G01N 33/00*    (2006.01)
*G01N 21/35*    (2014.01)

(52) U.S. Cl.
CPC .............. *G01N 21/59* (2013.01); *G01N 1/2247* (2013.01); *G01N 33/0054* (2013.01); *G01N 21/359* (2013.01); *G01N 21/3504* (2013.01)
USPC .......... 436/113; 436/106; 436/147; 436/164; 436/181; 422/82.05; 422/82.09; 422/83; 422/93

(58) Field of Classification Search
CPC ..... G01N 1/22; G01N 1/2247; G01N 1/2252; G01N 21/17; G01N 21/31; G01N 21/35; G01N 21/3504; G01N 21/359; G01N 21/59; G01N 33/0004; G01N 33/0009; G01N 33/0011; G01N 33/0013; G01N 33/0014; G01N 33/0022; G01N 33/0024; G01N 33/0036; G01N 33/0054; G01M 15/102; G01M 15/108
USPC ................. 436/106, 111, 113, 147, 164, 181; 422/82.05, 82.09, 82.12, 83, 93
See application file for complete search history.

(56) References Cited

U.S. PATENT DOCUMENTS 4,432,939 A * 2/1984 Watanabe et al. ............... 422/93
7,189,574 B2 * 3/2007 Owen et al. .................... 436/106
(Continued)

FOREIGN PATENT DOCUMENTS

CN    101285769 A    10/2008
JP    52-108198 A    9/1977
(Continued)

OTHER PUBLICATIONS

International Search Report for PCT/JP2010/066834, mailing date of Dec. 21, 2010.
(Continued)

*Primary Examiner* — Maureen Wallenhorst
(74) *Attorney, Agent, or Firm* — Westerman, Hattori, Daniels & Adrian, LLP

(57) ABSTRACT

An ammonia compound concentration measuring device includes: a pipe unit through which the circulating gas flows; a converter which is disposed in the pipe unit and converts an ammonia compound into ammonia; a measurement device which measures a first measurement value as a concentration of ammonia contained in a first circulating gas flowing inside a pipe line passing through the converter in the circulating gas flowing inside the pipe unit and a second measurement value as a concentration of ammonia contained in a second circulating gas flowing inside a pipe line not passing through the converter in the circulating gas flowing inside the pipe unit; and a controller which controls operations of the pipe unit and the measurement device and calculates the concentration of the ammonia compound of the measurement subject contained in the circulating gas from a difference between the first measurement value and the second measurement value.

13 Claims, 8 Drawing Sheets

(56) References Cited

U.S. PATENT DOCUMENTS

| | | | |
|---|---|---|---|
| 7,442,555 B2* | 10/2008 | Nair et al. ............... | 436/113 |
| 7,771,654 B1* | 8/2010 | Moore et al. ............. | 422/62 |
| 2003/0082816 A1 | 5/2003 | Guerra | |
| 2004/0225455 A1 | 11/2004 | Owen et al. | |
| 2006/0236752 A1 | 10/2006 | Nakamura | |
| 2010/0031730 A1 | 2/2010 | Van Uitert et al. | |

FOREIGN PATENT DOCUMENTS

| | | |
|---|---|---|
| JP | 53-100293 A | 9/1978 |
| JP | 56-79249 A | 6/1981 |
| JP | 57-40648 A | 3/1982 |
| JP | 7-110323 A | 4/1995 |
| JP | 10-38872 A | 2/1998 |
| JP | 10-142148 A | 5/1998 |
| JP | 2000-9603 A | 1/2000 |
| JP | 2000-97852 A | 4/2000 |
| JP | 3342446 B2 | 11/2002 |
| JP | 2003-185579 A | 7/2003 |
| JP | 2005-156296 A | 6/2005 |
| JP | 2006-275801 A | 10/2006 |
| JP | 2009-14421 A | 1/2009 |
| JP | 2010-509586 A | 3/2010 |
| KR | 10-2000-0006296 A | 1/2000 |

OTHER PUBLICATIONS

Translation of Written Opinion dated Dec. 12, 2010, issued in corresponding application No. PCT/JP2010/066834.
Korean Office Action dated Mar. 11, 2014, issued in corresponding Korean Application No. 10-2013-7033322 with English translation (20 pages).
Japanese Office Action dated Jun. 3, 2014, issued in corresponding Japanese Patent Application No. 2010-144300 with English translation (7 pages).
Chinese Office Action dated Jun. 4, 2014, issued in corresponding Chinese Patent Application No. 201080067588.2 with English translation (24 pages).
Notice of Allowance dated Aug. 26, 2014, issued in corresponding Korean Patent Application No. 10-2012-7033322, with Partial English Translation (3 pages).

* cited by examiner

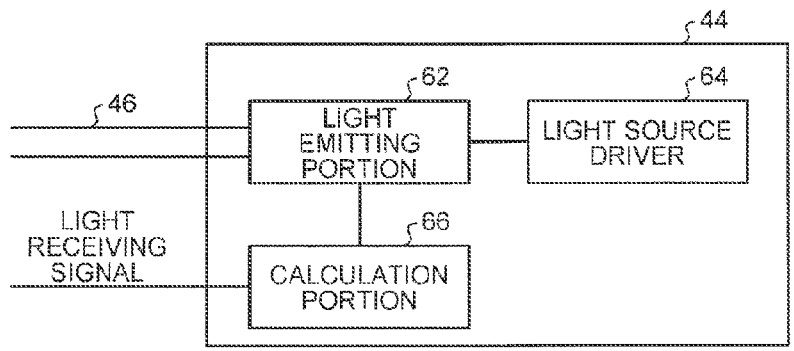
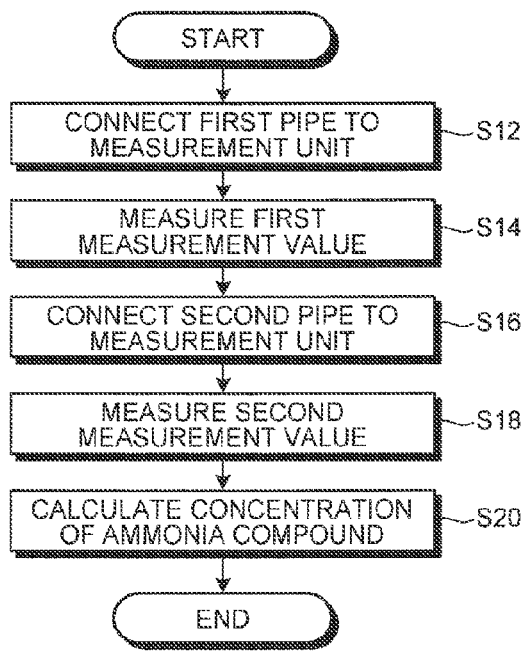

AMMONIA COMPOUND CONCENTRATION MEASURING DEVICE AND AMMONIA COMPOUND CONCENTRATION MEASURING METHOD

FIELD

The present invention relates to an ammonia compound concentration measuring device and an ammonia compound concentration measuring method that measure a concentration of an ammonia compound contained in a gas flowing inside a pipe line.

BACKGROUND

For example, a gas which is discharged from a combustion engine such as an internal-combustion engine and an incinerator becomes a mixture gas obtained by mixing various gaseous materials with one another. Such a flue gas flows inside a pipe line, and is supplied (discharged) to a predetermined device or an atmosphere. Here, as a method of measuring a concentration of an ammonia compound contained in the flue gas, there is known a method of wet-sampling the flue gas, collecting an ammonia element in a solution, and analyzing the collected solution by an indophenol absorption spectrophotometry, an ion chromatography analysis, or the like. As an example, "JISK0099" discloses a "method of analyzing ammonia in a flue gas".

Further, as a method of measuring a concentration of a specific material contained in the mixture gas (which is mainly a circulating gas) flowing inside the pipe line, there is known a method of causing a laser beam to pass through a predetermined path of a pipe line and measuring a concentration of a specific material in a measurement subject from the input and output thereof. For example, the present applicant has proposed Patent Literature 1, which discloses a gas concentration measurement device including a light source which oscillates a laser beam of an original absorption wavelength to a gaseous material as a measurement subject, a modulation unit which modulates the oscillation wavelength of the laser beam oscillated from the light source into at least two different frequencies, a guide unit which guides the laser beam modulated by the modulation unit to a measurement region where the gaseous material exists, a light receiving unit which receives the laser beam transmitted, reflected, or scattered in the measurement region, and a plurality of phase sensitive detectors which sequentially demodulate each of the modulated signals for each frequency in the signal received by the light receiving unit.

CITATION LIST

Patent Literature

Patent Literature 1: Japanese Patent No. 3342446

SUMMARY

Technical Problem

Here, in the measurement using the wet-sampling, not only the ammonia compound, but also the gaseous ammonia in the flue gas are collected. For this reason, the concentration of the sum of the ammonia compound and the gaseous ammonia is measured, and hence it is difficult to measure the concentration of the ammonia compound. Further, in the wet-sampling, the ammonia compound is collected into the solution, and the collected solution is analyzed. For this reason, there is a problem in which it takes time until the measurement value is calculated after the measurement starts.

Further, the device disclosed in Patent Literature 1 may measure the material of the measurement subject with high responsiveness. However, in the measurement method of measuring the absorption by the measurement subject by irradiating the near-infrared laser beam as in the device disclosed in Patent Literature 1, a part of the ammonia compound may not be measured.

The invention is made in view of such circumstances, and it is an object of the invention to provide an ammonia compound concentration measuring device and an ammonia compound concentration measuring method capable of simply and highly precisely measuring a concentration of an ammonia compound with high responsiveness.

Solution to Problem

According to an aspect of the present invention, an ammonia compound concentration measuring device which measures an ammonia compound concentration of a measurement subject contained in a circulating gas includes: a pipe unit through which the circulating gas flows; a converter which is disposed in the pipe unit and converts an ammonia compound contained in the circulating gas passing through the converter into ammonia; a measurement device which measures a first measurement value as a concentration of ammonia contained in a first circulating gas flowing inside a pipe line with the converter out of the circulating gas flowing inside the pipe unit, and measures a second measurement value as a concentration of ammonia contained in a second circulating gas flowing inside a pipe line without the converter out of the circulating gas flowing inside the pipe unit; and a controller which controls operations of the pipe unit and the measurement device, and calculates the concentration of the ammonia compound contained in the circulating gas from a difference between the first measurement value and the second measurement value. The measurement device includes a light emitting portion which outputs a laser beam having a wavelength absorbed by the ammonia and being in a near-infrared wavelength band, at least one measurement unit which includes a gas measurement cell causing the circulating gas to flow therethrough, an optical system causing a laser beam to be incident to the gas measurement cell, and a light receiving portion receiving the laser beam incident from the light emitting portion and passing through the gas measurement cell, and a calculation portion which calculates the measurement value of the ammonia of the circulating gas flowing through the gas measurement cell based on the intensity of the laser beam output from the light emitting portion and the intensity of the laser beam received by the light receiving portion.

According to the ammonia compound concentration measuring device, it is possible to highly precisely measure the concentration of the ammonia compound with high responsiveness.

Advantageously, the ammonia compound concentration measuring device further includes: a first flowmeter which is disposed at the upstream side in relation to the converter and measures a flow rate of the circulating gas flowing into the converter; and a second flowmeter which is disposed at the downstream side in relation to the converter and measures a flow rate of the circulating gas discharged from the converter. The controller corrects and calculates a measurement value of the ammonia of the circulating gas based on a measurement result of the first flowmeter and a measurement result of the second flowmeter. Accordingly, it is possible to measure the concentration of the ammonia compound contained in the circulating gas with the higher precision.

Advantageously, in the ammonia compound concentration measuring device, the pipe unit includes an inflow pipe into which the circulating gas flows, a first pipe which is connected to the downstream side end portion of the inflow pipe in the circulating gas flow direction and is provided with the converter, a second pipe which is connected to the downstream side end portion of the inflow pipe in the circulating gas flow direction together with the first pipe and is not provided with the converter, and a three-way valve which is connected to the downstream side end portion of the first pipe, the downstream side end portion of the second pipe, and the upstream side end portion of the gas measurement cell in the circulating gas flow direction. The controller connects the downstream side end portion of the first pipe to the upstream side end portion of the gas measurement cell in the circulating gas flow direction by the three-way valve so as to cause the first circulating gas to flow into the measurement device and measures the first measurement value, and the controller connects the downstream side end portion of the second pipe to the upstream side end portion of the gas measurement cell in the circulating gas flow direction by the three-way valve so as to cause the second circulating gas to flow into the measurement device, and measures the second measurement value. Accordingly, it is possible to perform the measurement by one measurement unit.

Advantageously, in the ammonia compound concentration measuring device, the pipe unit includes an inflow pipe into which the circulating gas flows, a first pipe which is connected to the downstream side end portion of the inflow pipe in the circulating gas flow direction and is provided with the converter, and a second pipe which is connected to the downstream side end portion of the inflow pipe in the circulating gas flow direction together with the first pipe and is not provided with the converter. The measurement device includes two measurement units, one measurement unit is disposed at the downstream side in relation to the converter in the circulating gas flow direction of the first pipe, and the other measurement unit is disposed in the first pipe. Accordingly, it is possible to continuously measure the ammonia compound.

Advantageously, in the ammonia compound concentration measuring device, the pipe unit includes an inflow pipe into which the circulating gas flows, and a retention pipe which is connected to the downstream side end portion of the inflow pipe in the circulating gas flow direction and is provided with the converter. The measurement device includes two measurement units, one measurement unit is disposed at the downstream side in relation to the converter in the circulating gas flow direction of the retention pipe, and the other measurement unit is disposed at the upstream side in relation to the converter in the circulating gas flow direction of the retention pipe. Accordingly, it is possible to continuously measure the ammonia compound.

Further, it is desirable that the converter be the thermal decomposition layer which converts the ammonia compound into the ammonia by an oxidization reaction. Accordingly, it is possible to convert the ammonia compound into a measureable material by a simple configuration.

Further, it is desirable that the converter be the thermal decomposition layer which thermally decomposes the ammonia compound into the ammonia. Accordingly, it is possible to further reliably convert the ammonia compound into the ammonia.

Advantageously, in the ammonia compound concentration measuring device, the converter includes a temperature adjusting portion which adjusts a temperature of the thermal decomposition layer. Accordingly, it is possible to further reliably convert the ammonia compound into the ammonia.

Advantageously, the ammonia compound concentration measuring device further includes a switching unit which selects an execution or a stop of the conversion operation of the converter. The pipe unit includes an inflow pipe into which the circulating gas flows, and a retention pipe which is connected to the downstream side end portion of the inflow pipe in the circulating gas flow direction and is provided with the converter. In the measurement device, the measurement unit is disposed at the downstream side in relation to the converter in the circulating gas flow direction of the retention pipe. The converter is a thermal decomposition layer which thermally decomposes an ammonia compound into ammonia. The switching unit is a temperature adjusting portion which adjusts a temperature of the thermal decomposition layer. The controller selects a state where the conversion operation of the converter is executed or a state where the conversion operation of the converter is stopped so as to select a state where the first circulating gas flows into the measurement unit or a state where the second circulating gas flows thereinto. Accordingly, it is possible to perform the measurement by one measurement unit.

Advantageously, in the ammonia compound concentration measuring device, the switching unit causes the temperature adjusting portion to heat the circulating gas up to a temperature at which the ammonia compound is decomposed so that the conversion operation of the converter is executed and to stop the heating of the circulating gas so that the conversion operation of the converter is stopped. Accordingly, it is possible to select whether to convert the ammonia compound into the ammonia by a simple operation. That is, it is possible to select the first circulating gas or the second circulating gas.

Advantageously, in the ammonia compound concentration measuring device, the converter further includes a collection layer which collects the ammonia compound. Accordingly, it is possible to further reliably convert the ammonia compound into the ammonia.

Advantageously, in the ammonia compound concentration measuring device, in the measurement unit, a laser beam passes inside a pipe which retains the converter. Accordingly, it is possible to form a part of the measurement cell as the pipe, and hence to further directly measure the circulating gas.

Advantageously, in the ammonia compound concentration measuring device, an entire amount of the circulating gas discharged from a device of the measurement subject flows inside the pipe unit. Accordingly, it is possible to measure the circulating gas with the higher precision.

Advantageously, in the ammonia compound concentration measuring device, the pipe unit collects a part of the circulating gas from a measurement subject pipe through which an entire amount of the circulating gas discharged from the device of the measurement subject flows. When the measurement is performed by the sampling in this way, it is possible to provide the measurement unit at an appropriate size.

According to another aspect of the present invention, an ammonia compound concentration measuring method which measures an ammonia compound concentration of a circulating gas flowing inside a pipe, includes: a first measurement step of outputting a laser beam having a wavelength absorbed by ammonia and being in a near-infrared wavelength band to a first circulating gas passing through a region provided with a converter for converting an ammonia compound into ammonia in the circulating gas flowing inside the pipe, receiving the laser beam passing through a pipe line through which the first circulating gas flows, and measuring a concentration of the ammonia contained in the first circulating gas as a first measurement value based on the intensity of the output laser beam and the intensity of the laser beam received by a light receiving portion; a second measurement step of outputting a laser beam having a wavelength absorbed by ammonia and being in a near-infrared wavelength band to a second circulating gas not passing through a region provided with a converter for converting an ammonia compound into ammonia in the circulating gas flowing inside the pipe, receiving the laser beam passing through a pipe line through which the second circulating gas flows, and measuring a concentration of the ammonia contained in the circulating gas as a second measurement value based on the intensity of the output laser beam and the intensity of the laser beam received by the light receiving portion; and a calculation step of calculating a measurement value of the concentration of the ammonia compound contained in the circulating gas from a difference between the first measurement value and the second measurement value.

According to the ammonia compound concentration measuring method, it is possible to highly precisely measure the concentration of the ammonia compound with high responsiveness.

Advantageous Effects of Invention

There is an effect that the ammonia compound concentration measuring device and the ammonia compound concentration measuring method according to the invention may highly precisely measure the concentration of the ammonia compound with high responsiveness.

BRIEF DESCRIPTION OF DRAWINGS

FIG. 2 is a block diagram illustrating a schematic configuration of a measurement device body of the ammonia compound concentration measuring device illustrated in FIG. 1.

FIG. 3 is a flowchart illustrating an operation of the ammonia compound concentration measuring device.

DESCRIPTION OF EMBODIMENTS

Hereinafter, an embodiment of an ammonia compound concentration measuring device and an ammonia compound concentration measuring method according to the invention will be described in detail based on the drawings. Further, the invention is not limited to the embodiment. Here, the ammonia compound concentration measuring device and the ammonia compound concentration measuring method may measure a concentration of an ammonia compound contained in a gas with respect to various gases flowing inside a pipe line. For example, the ammonia compound concentration measuring device and the ammonia compound concentration measuring method may measure a concentration of an ammonia compound contained in a flue gas while being applied to a pipe line through which the flue gas flows. Further, as a device equipped with a pipe line through which a flue gas flows, various combustion engines, for example, a vehicle, a ship, a power generator, an incinerator, and the like are exemplified. Specifically, the device and the method may be applied to a diesel engine so as to measure a concentration of an ammonia compound contained in a flue gas (a circulating gas) discharged from the diesel engine or a circulating gas discharged from a garbage incinerator. Further, a gas of a measurement subject is not limited to the flue gas discharged from the combustion device, and various circulating gases, for example, a combustion gas and a gas produced by an experiment or the like may be the measurement subject. Further, in the embodiment, an ammonia compound which exists in a circulating gas (a mixture gas) flowing inside a pipe becomes the measurement subject. Further, as the ammonia compound, ammonium sulfate $((NH_4)_2SO_4)$, ammonium hydrogen sulfate $((NH_4)HSO_4)$, and the like are exemplified. Further, the ammonia compound may include ammonium chloride $(NH_4Cl)$, ammonium perchlorate $(NH_4ClO_4)$, ammonium nitrate $(NH_4NO_3)$, ammonium carbonate $((NH_4)_4CO_3)$, and the like.

First Embodiment

Figure 1:
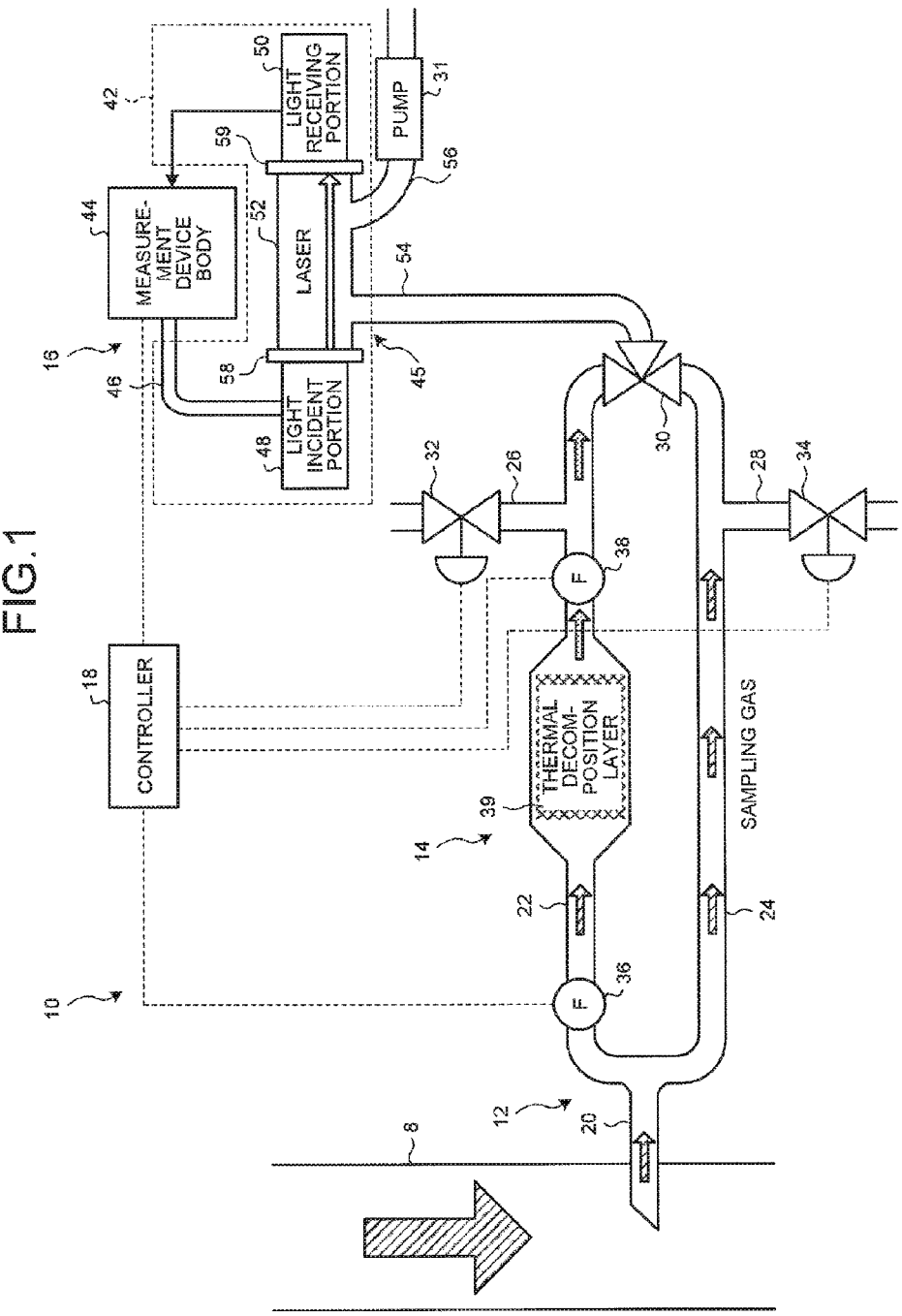
FIG. 1 is a schematic diagram illustrating a schematic configuration of an embodiment of an ammonia compound concentration measuring device.

FIG. 1 is a schematic diagram illustrating a schematic configuration of an embodiment of an ammonia compound concentration measuring device of the invention. An ammonia compound concentration measuring device 10 is a measuring device which extracts (samples) a part of a circulating gas flowing inside a measurement subject pipe 8 and measures a concentration of an ammonia compound contained in the circulating gas. The ammonia compound concentration measuring device 10 includes, as illustrated in FIG. 1, a pipe unit 12, a converter 14, a measurement device 16, and a controller 18. Further, the ammonia compound concentration measuring device 10 includes flowmeters 36 and 38.

The pipe unit 12 is connected to the measurement subject pipe 8 and constitutes a path that guides the circulating gas. The pipe unit 12 includes a sampling pipe (an inflow pipe) 20, a first pipe 22, a second pipe 24, branch pipes 26 and 28, a three-way valve 30, a pump 31, and opening and closing valves 32 and 34.

The sampling pipe (the inflow pipe) 20 is a pipe which is connected to the measurement subject pipe 8 and collects a part of the circulating gas flowing inside measurement subject pipe 8. In the sampling pipe 20, one end portion (the upstream side end portion in the circulating gas flow direction) is disposed inside the measurement subject pipe 8, and the other end portion (the downstream side end portion in the circulating gas flow direction) is disposed outside measurement subject pipe 8. Further, in order to reduce soot dust or the like contained in the collected circulating gas, the sampling pipe 20 is disposed so that an opening surface of one end portion is perpendicular to the circulating gas flow direction or faces the downstream side in the perpendicular direction. Further, the other end portion of the sampling pipe 20 is connected to two pipes, the first pipe 22 and the second pipe 24. Further, in the embodiment, a position where the circulating gas flows from the measurement subject pipe 8 into the sampling pipe 20 becomes the upstream side in the circulating gas flow direction. Further, the circulating gas which flows into the pipe unit 12 flows from one end portion of the sampling pipe 20 toward the other end portion thereof. A direction in which the circulating gas flowing from the measurement subject pipe 8 flows becomes the circulating gas flow direction.

In the first pipe 22, one end portion is connected to the sampling pipe 20 and the other end portion is connected to the three-way valve 30. Further, the converter 14 to be described later is disposed inside a pipe line of the first pipe 22. Further, in a region where the converter 14 is disposed in the first pipe 22, the diameter of the pipe line is larger than those of the other regions. Further, in the embodiment, the diameter of the pipe line of the region where the converter 14 is disposed is large, but the diameter of the pipe line may be constant.

Further, in the first pipe 22, the branch pipe 26 is installed at the downstream side in the circulating gas flow direction in relation to the converter 14. Further, the branch pipe 26 is provided with the opening and closing valve 32. Further, the downstream side of the branch pipe 26 in the circulating gas flow direction may be opened to the external air, but when the circulating gas contains a toxic element and the like, it is desirable to connect the branch pipe to a treatment device which treats the circulating gas or the downstream side of the measurement subject pipe 8.

The second pipe 24 is a pipe which is basically formed in parallel to the first pipe 22, where one end portion is connected to the sampling pipe 20 and the other end portion is connected to the three-way valve 30. Further, the converter 14 to be described later is not disposed inside the pipe line of the second pipe 24.

Further, the second pipe 24 is also provided with the branch pipe 28. Further, it is desirable to install the branch pipe 28 at a position corresponding to the branch pipe 26 in the circulating gas flow direction. Further, the branch pipe 28 is provided with the opening and closing valve 34. Further, the downstream side of the branch pipe 28 in the circulating gas flow direction may be also opened to the external air, but when the circulating gas contains a toxic element and the like, it is desirable to connect the branch pipe to a treatment device which treats the circulating gas or the downstream side of the measurement subject pipe 8.

The three-way valve 30 connects the downstream side end portion of the first pipe 22, the downstream side end portion of the second pipe 24, and the upstream side end portion of the measurement device 16 to each other. The three-way valve 30 selects a state where the first pipe 22 is connected to the measurement device 16 or a state where the second pipe 24 is connected to the measurement device 16. When the three-way valve 30 connects the first pipe 22 to the measurement device 16, the circulating gas which passes from the sampling pipe 20 to the first pipe 22 flows to the measurement device 16. Further, when the three-way valve 30 connects the second pipe 24 to the measurement device 16, the circulating gas which passes from the sampling pipe 20 to the second pipe 24 flows to the measurement device 16. In this way, the three-way valve 30 changes the circulating gas which flows to the measurement device 16.

The pump 31 is disposed at the downstream side of the measurement device 16 in the circulating gas flow direction. The pump 31 suctions air in a direction in which the circulating gas flows from the sampling pipe 20 toward the measurement device 16.

The converter 14 is a mechanism which converts an ammonia compound of a measurement subject contained in the circulating gas into ammonia, and is disposed inside the pipe line of the first pipe 22. The converter 14 includes a thermal decomposition layer 39 which is disposed inside the pipe line of the first pipe 22. The thermal decomposition layer 39 thermally decomposes the passing circulating gas and the ammonia compound contained in the circulating gas at a predetermined temperature or more, so that they are converted into ammonia. Further, the materials combined with the ammonia are separated from the ammonia, and become other materials. The configuration of the thermal decomposition layer 39 is not limited as long as the passing ammonia compound may become a predetermined temperature or more. For example, as the thermal decomposition layer 39, a combination of a pipe and an image furnace for heating a circulating gas flowing inside the pipe may be used. Further, as the heating mechanism, the mechanism is not limited to the image furnace, and various heating mechanisms may be used. For example, a mechanism which heats a circulating gas by heating a pipe through a combustion of a combustion gas at the outer periphery of the pipe or a mechanism which heats a circulating gas by forming a pipe as a double-type pipe, causing the circulating gas to flow through the inner pipe, and causing a heated fluid to flow through the outer pipe. Further, it is desirable that the thermal decomposition layer 39 heat the ammonia compound to 300° C. or more in order to appropriately thermally decompose the ammonia compound. Further, as for the temperature at which the ammonia compound is heated by the thermal decomposition layer 39 of the converter 14, the temperature is not particularly limited as long as the ammonia compound may be decomposed into ammonia and other materials. Further, the thermal decomposition layer 39 of the converter 14 heats the circulating gas and the ammonia compound in a temperature range in which the ammonia is not converted into other materials. Further, it is desirable that the thermal decomposition layer 39 heat the circulating gas without supplying a fluid thereto.

The measurement device 16 is a measurement device which measures a concentration of the ammonia contained in the circulating gas flowing inside the pipe line (flowing from the three-way valve 30), and includes a measurement unit 42 which causes the circulating gas to flow through a predetermined pipe line and causes a laser beam (a laser) to pass therethrough and a measurement device body 44 which supplies a laser beam to the measurement unit 42 and calculates a measurement value from the intensity of the received laser beam.

The measurement unit 42 includes a measurement cell 45, an optical fiber 46, a light incident portion 48, and a light receiving portion 50.

The measurement cell 45 basically includes a main pipe 52, an inflow pipe 54, and a discharge pipe 56. The main pipe 52 is a cylindrical member, and the circulating gas flows therein. A window 58 is disposed at one end portion (upper surface) of the cylindrical main pipe 52 and a window 59 is disposed at the other end portion (lower surface). That is, the cylindrical upper and lower surfaces of the main pipe 52 are respectively blocked by the window 58 and the window 59. Further, the windows 58 and 59 are formed by a light transmitting member, for example, a transparent glass, a resin, or the like. Accordingly, both end portions of the main pipe 52 provided with the windows 58 and 59 may cause the light to be transmitted therethrough while the circulation of air is not permitted. That is, the light may be incident from the outside of the main pipe 52 into the main pipe, and the light may be emitted to the outside from the inside of the main pipe 52.

In the inflow pipe 54, one end portion is connected to the three-way valve 30 and the other end portion is connected to the side of the window 58 of the side surface (the peripheral surface) of the main pipe 52. In the discharge pipe 56, one end portion is connected to the side of the window 59 of the side surface (the peripheral surface) of the main pipe 52 and the other end portion is connected to the pipe disposed at the farther downstream side (the pipe in which the pump 31 is disposed). The measurement cell 45 supplies the circulating gas, supplied from the first pipe 22 or the second pipe 24 through the three-way valve 30, from the inflow pipe 54 to the main pipe 52. Further, the measurement cell 45 discharges the circulating gas which flows inside the main pipe 52 from the discharge pipe 56 to the outside.

Next, the optical fiber 46 guides the laser beam output from the measurement device body 44 to the light incident portion 48. That is, the laser beam which is output from the measurement device body 44 is incident to the light incident portion 48. The light incident portion 48 is an optical system (a mirror, a lens, and the like) which is disposed in the window 58, and causes the laser beam guided by the optical fiber 46 to be incident from the window 58 into the main pipe 52.

The light receiving portion 50 is a light receiving portion which receives the laser beam passing through the main pipe 52 of the measurement cell 45 and output from the window 59. Further, the light receiving portion 50 includes, for example, an optical detector such as a photodiode (PD) and receives the laser beam by the optical detector so as to detect the intensity of the light. The light receiving portion 50 transmits the intensity of the received laser beam as a light receiving signal to the measurement device body 44.

Next, the measurement device body 44 will be described by using FIGS. 1 and 2. Here, FIG. 2 is a block diagram illustrating a schematic configuration of the measurement device body of the ammonia compound concentration measuring device illustrated in FIG. 1. The measurement device body 44 includes a light emitting portion 62, a light source driver 64, and a calculation portion 66.

The light emitting portion 62 is a light emitting element which emits a laser beam of a near-infrared wavelength band which is absorbed by the ammonia. As the light emitting element, for example, a laser diode (LD) may be used. The light emitting portion 62 causes the emitted light to be incident to the optical fiber 46.

The light source driver 64 has a function of controlling the driving of the light emitting portion 62, and adjusts the wavelength and the intensity of the laser beam which is output from the light emitting portion 62 by adjusting the current and the voltage supplied to the light emitting portion 62.

The calculation portion 66 calculates the concentration of the material of the measurement subject based on the signal of the intensity of the laser beam received by the light receiving portion 50 and the condition for driving the light source driver 64. Specifically, the calculation portion 66 calculates the intensity of the laser beam which is output from the light emitting portion 62 and is incident to the main pipe 52 based on the condition for driving the light source driver 64, compares the calculated intensity with the intensity of the laser beam received by the light receiving portion 50, and calculates the concentration of the materials (the ammonia, the materials produced by converting (decomposing) the ammonia compound) of the measurement subject contained in the circulating gas flowing inside the main pipe 52.

The measurement device 16 has the above-described configuration, and the laser beam of the near-infrared wavelength band output from the light emitting portion 62 reaches the light receiving portion 50 after passing through a predetermined path from the optical fiber 46 to the measurement cell 45, and specifically, the window 58, the main pipe 52, and the window 59. At this time, when the material (ammonia) of the measurement subject is contained in the circulating gas inside measurement cell 45, the laser beam which passes through the measurement cell 45 is absorbed. For this reason, in the laser beam, the output of the laser beam which reaches the light receiving portion 50 changes by the concentration of the material of the measurement subject in the circulating gas. The light receiving portion 50 converts the received laser beam into a light receiving signal and outputs the signal to the calculation portion 66. Further, the light source driver 64 outputs the intensity of the laser beam output from the light emitting portion 62 to the calculation portion 66. The calculation portion 66 compares the intensity of the light output from the light emitting portion 62 with the intensity calculated from the light receiving signal, and calculates the concentration of the material of the measurement subject of the circulating gas flowing inside the measurement cell 45 from the reduction rate. In this way, the measurement device 16 calculates and/or measures the concentration of the material of the measurement subject in the circulating gas passing through a predetermined position, that is, a measurement position inside the main pipe 52 based on the intensity of the output laser beam and the light receiving signal detected by the light receiving portion 50 by using a so-called TDLAS method (Tunable Diode Laser Absorption Spectroscopy). Further, the measurement device 16 may continuously calculate and/or measure the concentration of the material of the measurement subject.

Here, the flowmeter 36 is disposed at the upstream side in relation to the converter 14 of the first pipe 22, and measures the flow rate of the circulating gas flowing inside the first pipe 22. The flowmeter 36 measures the flow rate of the circulating gas which is about to pass through the converter 14 (the thermal decomposition layer 39), that is, the circulating gas which is about to undergo the conversion (the thermal decomposition) of the ammonia compound in the first circulating gas flowing inside the first pipe 22. Further, the flowmeter 38 is disposed at the downstream side in relation to the converter 14 of the first pipe 22, and measures the flow rate of the circulating gas flowing inside the first pipe 22. The flowmeter 38 measures the flow rate of the circulating gas which passes through the converter 14 (the thermal decomposition layer 39), that is, the circulating gas which undergoes the conversion of the ammonia compound in the first circulating gas flowing inside the first pipe 22. The flowmeters 36 and 38 transmit the measured flow rates to the controller 18.

The controller 18 has a function of controlling the operations of the pipe unit 12, the converter 14, the measurement device 16, and the flowmeters 36 and 38, and controls the operations of the respective constituents if necessary. Specifically, the controller 18 controls the measurement condition using the measurement device 16 (the driving condition of the light source driver 64 and the light receiving operation of the light receiving portion 50), the path selecting operation of the three-way valve 30 of the pipe unit 12, and the opening and closing operations of the opening and closing valves 32 and 34. Further, the controller 18 calculates and/or measures the concentration of the ammonia compound of the measurement subject based on the measurement result (that is, the concentration of the ammonia) measured by the measurement device 16, the settings and the detecting conditions of the respective constituents, and the flow rates measured by the flowmeters 36 and 38.

Next, an operation of the ammonia compound concentration measuring device 10 will be described. Here, FIG. 3 is a flowchart illustrating the operation of the ammonia compound concentration measuring device. When an instruction for starting the measurement is input while the circulating gas flows inside measurement subject pipe 8, the controller 18 of the ammonia compound concentration measuring device 10 drives the pump 31 so as to suction the circulating gas flowing inside measurement subject pipe 8 from the sampling pipe 20. Further, it is desirable to open the opening and closing valves 32 and 34 at this time. Further, the three-way valve 30 may be connected to any pipe line, but it is desirable that the three-way valve alternately switch a state where the pipe connected to the measurement unit 42 is connected to the first pipe 22 and a state where the pipe connected to the measurement unit 42 is connected to the second pipe 24.

Subsequently, when the circulating gas flows inside the pipe unit 12 so that the pipe unit 12 is filled with the circulating gas, in step S12, the controller 18 connects the first pipe 22 to the measurement unit 42 by the three-way valve 30, so that the circulating gas flowing inside the first pipe 22, that is, the circulating gas flowing through the converter 14 (the circulating gas which is subjected to the conversion of the ammonia compound, and hereinafter, referred to as the "first circulating gas") flows to the measurement unit 42. Further, the opening and closing valve 32 is closed at this time, so that the entire amount of the circulating gas flowing inside the first pipe 22 is supplied to the measurement unit 42. Further, the opening and closing valve 34 may be opened or closed. Further, the flowmeters 36 and 38 measure the flow rate of the first circulating gas flowing through the measurement position of the first pipe 22.

When the first circulating gas flows through the measurement cell 45, in step S14, the controller 18 measures the concentration of the ammonia (hereinafter, referred to as the "first measurement value") which is contained in the first circulating gas flowing inside the main pipe 52 of the measurement cell 45 of the measurement unit 42 by the measurement device 16. Accordingly, it is possible to measure the concentration of the ammonia contained in the first circulating gas by the converter 14. Further, the first circulating gas contains the ammonia which is converted from the ammonia compound of the measurement subject by the converter 14 and the ammonia (the coexistent gas) which is contained before the conversion. For this reason, as the first measurement value, the concentration is measured that is obtained by adding the ammonia (the ammonia derived from the ammonia compound of the measurement subject contained in the circulating gas) converted from the ammonia compound of the measurement subject by the thermal decomposition layer 39 and the ammonia (the coexistent gas) contained before the conversion.

When the concentration of the first circulating gas is measured, in step S16, the controller 18 connects the second pipe 24 to the measurement unit 42 by the three-way valve 30, so that the circulating gas flowing inside the second pipe 24 (the circulating gas which is not subjected to the conversion of the ammonia compound, and hereinafter, referred to as the "second circulating gas") flows to the measurement unit 42. Furthermore, the opening and closing valve 34 is closed at this time, so that the entire amount of the circulating gas flowing inside the second pipe 24 is supplied to the measurement unit 42. Further, the opening and closing valve 32 may be opened or closed.

When the second circulating gas flows through the measurement cell 45, in step S18, the controller 18 measures the concentration of the ammonia (hereinafter, referred to as the "second measurement value") contained in the second circulating gas flowing inside the main pipe 52 of the measurement cell 45 of the measurement unit 42 by the measurement device 16. Accordingly, the concentration of the ammonia contained in the second circulating gas may be measured by the converter 14. Further, the second circulating gas contains the ammonia (the coexistent gas) contained before the conversion. For this reason, as the second measurement value, the concentration of the ammonia (the coexistent gas) contained before the conversion is measured.

When the concentration of the second circulating gas is measured, in step S20, the controller 18 calculates the concentration (the measurement value) of the ammonia compound contained in the circulating gas. Specifically, the measurement value of the ammonia compound contained in the circulating gas is calculated by a difference between the first measurement value measured in step S14 and the second measurement value measured in step S18. That is, it is possible to calculate the concentration of the ammonia derived from the ammonia compound contained in the circulating gas by subtracting the concentration of the coexistent gas from the concentration obtained by adding the coexistent gas and the ammonia derived from the ammonia compound of the measurement subject contained in the circulating gas. Further, the controller 18 may calculate the concentration of the ammonia compound of the measurement subject contained in the circulating gas by adding (correcting) a relation between the flow rate of the circulating gas and the ammonia derived from the ammonia compound contained in the circulating gas and an increase and a decrease in amount of each element by the process of the reaction from the ammonia compound into the ammonia based on the information supplied from the flowmeters 36 and 38 and the like. When the measurement value of the ammonia compound is calculated, the controller 18 ends the present process. Further, the controller 18 may continuously measure the concentration of the ammonia compound by repeating the above-described process.

As described above, the ammonia compound concentration measuring device 10 measures the concentration of the ammonia contained in the first circulating gas which is subjected to the conversion of the ammonia compound of the measurement subject by the converter 14 through the measurement device 16, measures the concentration of the ammonia contained in the second circulating gas which is not subjected to the conversion of the ammonia compound of the measurement subject through the measurement device 16, and obtains a difference therebetween, thereby calculating the concentration of the ammonia compound of the measurement subject.

Further, the ammonia compound concentration measuring device 10 may measure, through the measurement device 16, the concentration of the ammonia compound in a short time with high precision by irradiating the laser beam of the near-infrared wavelength band of the absorption wavelength band of the converted material (the decomposed material, the ammonia obtained by converting the ammonia compound) of the ammonia compound of the measurement subject and detecting the intensity absorbed by the ammonia.

Further, when the ammonia compound of the measurement subject is converted and the converted material (ammonia) is measured, it is possible to measure the concentration of the ammonia compound without the absorption wavelength in the near-infrared wavelength band by using the semiconductor laser absorption spectroscopic process illustrated in the measurement device 16. Further, since the measurement using the light of the wavelength of the near-infrared band of the material of the measurement subject may be performed as in the embodiment, the high-precision measurement may be performed. Further, even when the ammonia compound is formed by a plurality of compounds, it is possible to measure the concentration of the ammonia compound contained in the circulating gas just by measuring the ammonia.

Furthermore, in the measurement using the laser beam of the near-infrared wavelength band, it is possible to appropriately measure the concentration of the converted material of the measurement subject even when there are elements other than the converted material (ammonia) of the measurement subject. That is, the elements other than the converted material of the measurement subject may not easily serve as noise. Accordingly, it is possible to remove a filter or a dehumidification process or decrease the number of steps included in the dehumidification process. As a result, it may take a short time until the measurement result is calculated by the measurement after suctioning the circulating gas from the measurement subject pipe 8. That is, a delay in measurement time may be reduced. Accordingly, the responsiveness may be improved.

Further, the ammonia compound concentration measuring device 10 may further appropriately calculate the concentration of the ammonia compound contained in the circulating gas by calculating the flow rates before and after the converter 14 and correcting an influence caused by a change in mass balance and a change in the number of moles by the conversion (thermal decomposition) based on a change in flow rate. Further, it is desirable to measure a change in the flow rate before and after the converter as in the embodiment in order to further appropriately correct the concentration of the ammonia compound, but the invention is not limited thereto. The correction may not be performed. Further, a change in flow rate may be estimated from a relation between the first measurement value and the second measurement value, and the correction may be performed based on the estimated value.

Further, the ammonia compound concentration measuring device 10 may also measure the concentration of the coexistent gas contained in the circulating gas, that is, the ammonia originally contained in the circulating gas. Accordingly, a ratio between the ammonia compound and the ammonia contained in the circulating gas may be calculated.

Further, since the pump 31 is provided, it is possible to appropriately suction the circulating gas flowing inside measurement subject pipe 8 from the sampling pipe 20. Further, it is desirable to provide the pump 31, but when the circulating gas of a predetermined flow rate or more flows to the pipe unit 12 due to the configuration of the pipe unit 12, the pressure of the circulating gas flowing inside measurement subject pipe 8, and the like, the pump 31 may not be provided.

Here, the ammonia compound concentration measuring device is not limited to the above-described embodiment, and various embodiments may be used. Hereinafter, another embodiment will be described by using FIGS. 4 to 9.

Second Embodiment

Figure 4:
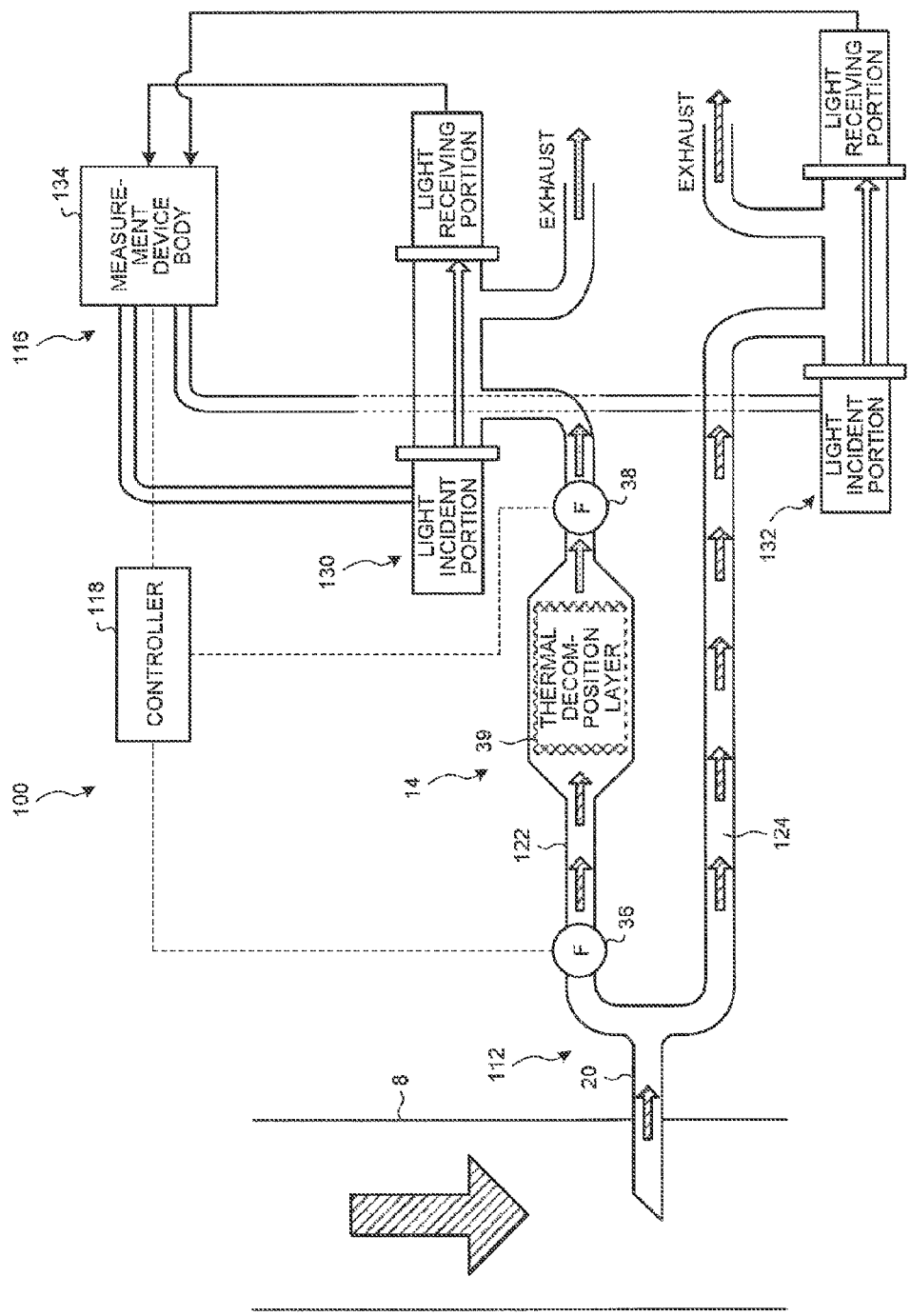
FIG. 4 is a schematic diagram illustrating a schematic configuration of another embodiment of the ammonia compound concentration measuring device.

FIG. 4 is a schematic diagram illustrating a schematic configuration of another embodiment of the ammonia compound concentration measuring device. An ammonia compound concentration measuring device 100 illustrated in FIG. 4 includes a pipe unit 112, the converter 14, a measurement device 116, a controller 118, and the flowmeters 36 and 38. Here, in the ammonia compound concentration measuring device 100, two measurement units are installed, and the measurement units are respectively disposed in a first pipe 122 and a second pipe 124. Further, since the converter 14 and the flowmeters 36 and 38 have the same configurations as those of the converter 14 and the flowmeters 36 and 38 illustrated in FIG. 1, the description thereof will not be repeated.

The pipe unit 112 includes the sampling pipe 20, the first pipe 122, and the second pipe 124. Since the sampling pipe 20 has the same configurations as those of the respective portions of the pipe unit 12, the description thereof will not be repeated.

In the first pipe 122, one end portion is connected to the sampling pipe 20 and the other end portion is connected to a first measurement unit 130 of the measurement device 116. Further, the converter 14 is disposed inside the pipe line of the first pipe 122. Further, in a region where the converter 14 is disposed in the first pipe 122, the diameter of the pipe line is larger than those of the other regions.

The second pipe 124 is a pipe which is basically formed in parallel to the first pipe 122, where one end portion is connected to the sampling pipe 20 and the other end portion is connected to a second measurement unit 132 of the measurement device 116. Further, the converter 14 is not disposed inside the pipe line of the second pipe 124. In this way, the pipe unit 112 is not provided with the three-way valve which connects the other end portion of the first pipe 122 to the other end portion of the second pipe 124, and is connected to another measurement unit.

The measurement device 116 includes the first measurement unit 130, the second measurement unit 132, and a measurement device body 134. The first measurement unit 130 is connected to the other end portion of the first pipe 122, and the circulating gas flowing inside the first pipe 122, that is, the circulating gas (the first circulating gas) passing through the converter 14 is supplied thereto. Further, since the configurations of the respective constituents of the first measurement unit 130 are the same as those of the measurement unit 42, the detailed description thereof will not be repeated.

The second measurement unit 132 is connected to the other end portion of the second pipe 124, and the circulating gas flowing inside the second pipe 124, that is, the circulating gas (the second circulating gas) which does not pass through the converter 14 is supplied thereto. Further, since the configurations of the respective constituents of the second measurement unit 132 are also the same as those of the measurement unit 42, the detailed description thereof will not be repeated.

The measurement device body 134 basically has the same configuration as that of the measurement device body 44 except that the laser beam is output to two measurement units, the first measurement unit 130 and the second measurement unit 132, and the light receiving signals are received from two measurement units. Furthermore, the measurement device body 134 may be provided with two light emitting portions and the laser beams may be emitted to the respective measurement units. However, it is desirable that the laser beam output from one light emitting portion be branched into two laser beams and the laser beams are output to the respective measurement units. Since one light emitting portion is provided, the wavelengths of the laser beams incident to two measurement units may be made to be equal to each other, and hence the measurement precision may be further improved.

The measurement device body 134 measures the concentration of the ammonia contained in the first circulating gas (the circulating gas which is subjected to the conversion of the ammonia compound) based on the intensity of the laser beam output to the first measurement unit 130 and the light receiving signal transmitted from the first measurement unit 130, and measures the concentration of the ammonia contained in the second circulating gas (the circulating gas which is not subjected to the conversion of the ammonia compound) based on the intensity of the laser beam output to the second measurement unit 132 and the light receiving signal transmitted from the second measurement unit 132. The measurement device body 134 transmits the measurement result to the controller 118.

The controller 118 controls the operations of the respective constituents of the pipe unit 112, the converter 14, and the measurement device 116 as in the controller 18. Further, the controller 118 measures (calculates) the concentration of the ammonia compound contained in the circulating gas based on the measurement result transmitted from the measurement device 116. Further, the calculation method is the same as the calculation method of the controller 18.

With the above-described configuration, the ammonia compound concentration measuring device 100 may measure the concentration of the ammonia compound of the measurement subject contained in the circulating gas. Further, as in the ammonia compound concentration measuring device 10, a so-called TDLAS-type measurement device is used as the measurement device and the concentration of the material (ammonia) obtained by converting the ammonia compound is set as the measurement subject using the measurement device, thereby obtaining the same effect as described above.

Since the ammonia compound concentration measuring device 100 is provided with two measurement units, the first measurement unit 130 and the second measurement unit 132, the first circulating gas and the second circulating gas may be separately measured. Accordingly, the concentration of the ammonia contained in the first circulating gas and the concentration of the ammonia contained in the second circulating gas may be measured at the same time. Accordingly, there is no need to change the passageway, and hence it is possible to further continuously measure the concentration of the ammonia compound of the measurement subject contained in the circulating gas. Further, since the measurement may be performed without changing the passageway, the responsiveness of the measurement may be also further improved.

Further, as described above, the concentration of the ammonia compound may be corrected based on the measurement results of the flowmeter 36 and the flowmeter 38.

Third Embodiment

Figure 5:
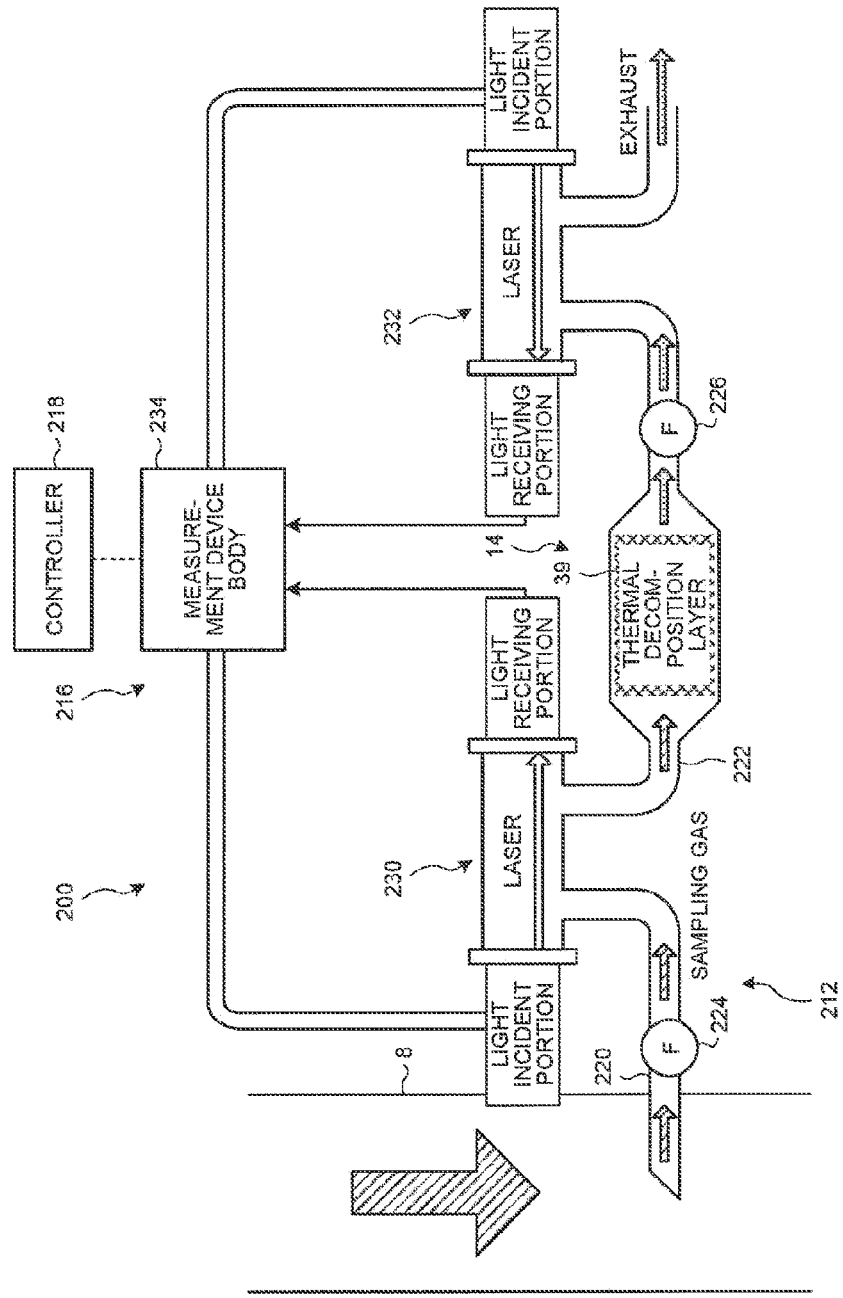
FIG. 5 is a schematic diagram illustrating a schematic configuration of another embodiment of the ammonia compound concentration measuring device.

FIG. 5 is a schematic diagram illustrating a schematic configuration of another embodiment of the ammonia compound concentration measuring device. An ammonia compound concentration measuring device 200 illustrated in FIG. 5 includes a pipe unit 212, the converter 14, a measurement device 216, a controller 218, and flowmeters 224 and 226. Here, in the ammonia compound concentration measuring device 200, the pipe unit is formed as one pipe and two measurement units are installed. Further, since the converter 14 has the same configuration as that of the converter 14 illustrated in FIG. 1, the description thereof will not be repeated.

The pipe unit 212 includes a sampling pipe 220, a pipe 222, and the flowmeter 224. The sampling pipe 220 is a pipe which is connected to the measurement subject pipe 8 and collects a part of the circulating gas flowing inside measurement subject pipe 8, where one end portion is disposed inside measurement subject pipe 8 and the other end portion is connected to an upstream side measurement unit 230 of the measurement device 216.

In the pipe 222, one end portion is connected to the upstream side measurement unit 230 and the other end portion is connected to a downstream side measurement unit 232 of the measurement device 216. Further, the converter 14 is disposed inside the pipe line of the pipe 222. Further, in a region where the converter 14 is disposed in the pipe 222, the diameter of the pipe line is larger than those of the other regions.

The measurement device 216 includes the upstream side measurement unit 230, the downstream side measurement unit 232, and a measurement device body 234. In the upstream side measurement unit 230, the upstream side end portion is connected to the other end portion of the sampling pipe 220 and the downstream side end portion is connected to one end portion (the upstream side end portion) of the pipe 222. Then, the circulating gas (the circulating gas which is not subjected to the conversion of the ammonia compound, the second circulating gas) which flows inside the sampling pipe 220 and does not pass through the converter 14 yet is supplied thereto. Further, since the upstream side measurement unit 230 is the same as the measurement unit 42, the detailed description thereof will not be repeated.

In the downstream side measurement unit 232, the upstream side end portion is connected to one end portion (the downstream side end portion) of the pipe 222 and the downstream side end portion is connected to the farther downstream side pipe (the exhaust pipe or the like). Then, the circulating gas (the circulating gas which is subjected to the conversion of the ammonia compound, the first circulating gas) which flows inside the pipe 222 and passes through the converter 14 is supplied thereto. Further, since the downstream side measurement unit 232 is also the same as the measurement unit 42, the detailed description thereof will not be repeated.

The measurement device body 234 basically has the same configuration as that of the measurement device body 44 except that the laser beam is output to two measurement units, the upstream side measurement unit 230 and the downstream side measurement unit 232, and the light receiving signals from two measurement units are received. That is, the measurement device body has the same configuration as that of the measurement device body 134.

The measurement device body 234 measures the concentration of the ammonia contained in the first circulating gas based on the intensity of the laser beam output from the downstream side measurement unit 232 and the light receiving signal transmitted from the downstream side measurement unit 232 and measures the concentration of the ammonia contained in the second circulating gas based on the intensity of the laser beam output from the upstream side measurement unit 230 and the light receiving signal transmitted from the upstream side measurement unit 230. The measurement device body 234 transmits the measurement result to the controller 218.

Further, the flowmeter 224 is disposed on the path of the sampling pipe 220, and measures the flow rate of the circulating gas flowing inside the sampling pipe 220, that is, the flow rate of the circulating gas (the second circulating gas) which does not pass through the converter 14 yet. Further, the flowmeter 226 is disposed between the converter 14 of the pipe 222 and the downstream side measurement unit 232, and measures the flow rate of the circulating gas (the first circulating gas) which passes through the converter 14.

The controller 218 controls the operations of the respective constituents of the pipe unit 212, the converter 14, and the measurement device 216 as in the controller 18. Further, the controller 218 measures (calculates) the concentration of the ammonia compound of the measurement subject contained in the circulating gas based on the measurement result transmitted from the measurement device 216. Further, the calculation method is the same as the calculation method of the controller 18.

With the above-described configuration, the ammonia compound concentration measuring device 200 may measure the concentration of the ammonia compound of the measurement subject contained in the circulating gas even when the measurement units are respectively provided at the upstream side and the downstream side of the region where the converter 14 (the thermal decomposition layer 39) is disposed. Further, as in the ammonia compound concentration measuring device 10, a so-called TDLAS-type measurement device is used as the measurement device and the concentration of the material (ammonia) obtained by converting (thermally decomposing) the ammonia compound of the measurement subject is set as the measurement subject using the measurement device, thereby obtaining the same effect as described above.

The ammonia compound concentration measuring device 200 may separately measure the first circulating gas and the second circulating gas without separating the pipe for guiding the circulating gas into two pipes by installing two measurement units, the measurement units 230 and 232 at the upstream side and the downstream side of a region where the thermal decomposition layer 39 is disposed. Further, even in this case, it is possible to measure the concentration of the ammonia contained in the first circulating gas and the concentration of the ammonia contained in the second circulating gas at the same time. Accordingly, there is no need to change the passageway, and hence it is possible to further continuously measure the concentration of the ammonia compound of the circulating gas (the concentration of the ammonia compound contained in the circulating gas). Further, since the measurement may be performed without changing the passageway, the responsiveness of the measurement may be also further improved. Further, the gas of the measurement subject may be set as the same circulating gas. That is, the circulating gas measured by the upstream side measurement unit 230 may be converted (thermally decomposed), and then may be measured by the downstream side measurement unit 232. Further, it is possible to detect a change in the balance of the number of moles between the circulating gas (the second circulating gas) which does not pass through the converter 14 yet and the circulating gas (the first circulating gas) which passes through the converter 14 by the flowmeter 224 and the flowmeter 226. Accordingly, it is possible to correct the calculation value of the concentration of the ammonia compound of the circulating gas from the calculated number of moles, and hence to further precisely measure the concentration of the ammonia compound.

Fourth Embodiment

Figure 6:
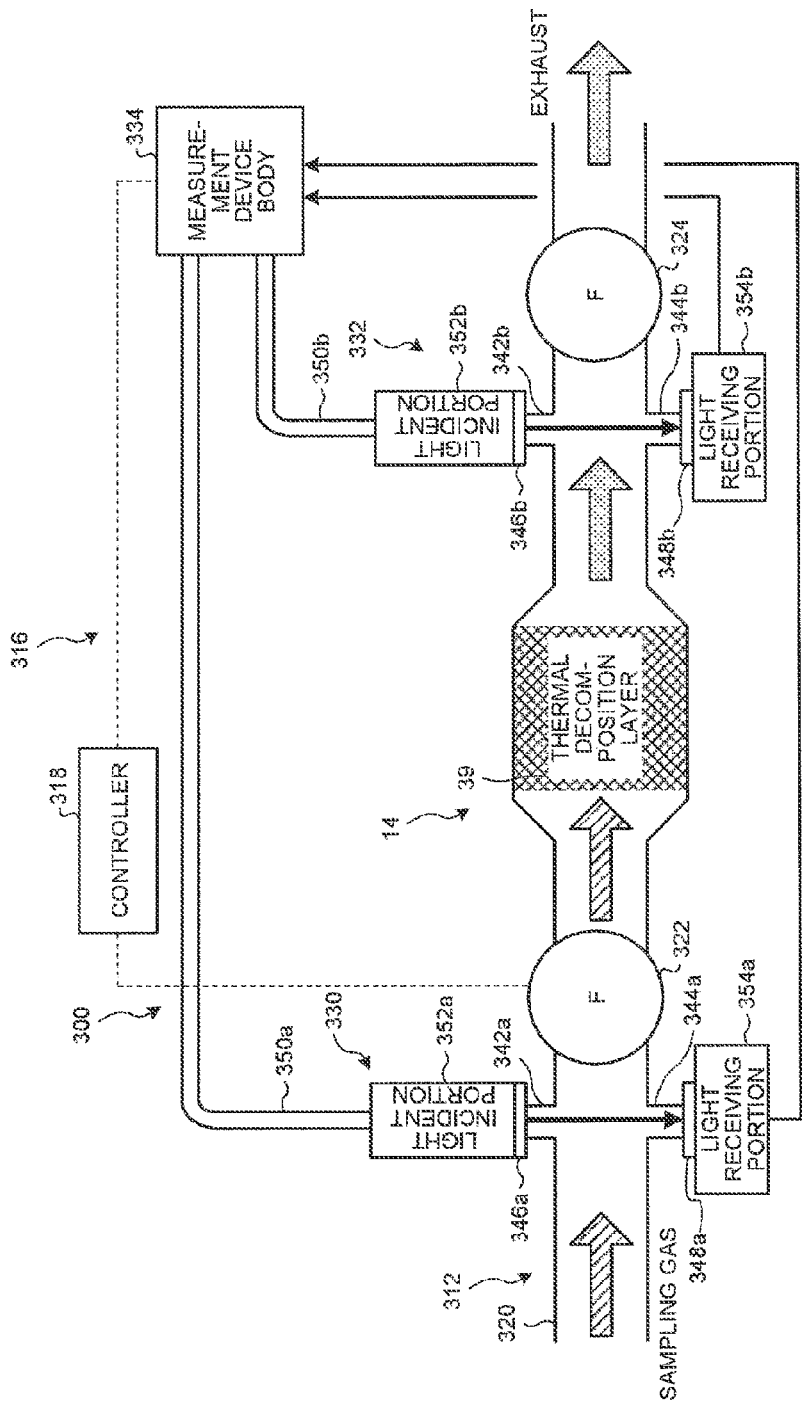
FIG. 6 is a schematic diagram illustrating a schematic configuration of another embodiment of the ammonia compound concentration measuring device.

FIG. 6 is a schematic diagram illustrating a schematic configuration of another embodiment of the ammonia compound concentration measuring device. An ammonia compound concentration measuring device 300 illustrated in FIG. 6 includes a pipe unit 312, the converter 14, a measurement device 316, a controller 318, and flowmeters 322 and 324. Here, the ammonia compound concentration measuring device 300 has the same configuration as that of the ammonia compound concentration measuring device 200 except for the configuration of the pipe unit 312 and the arrangement position and the configuration of the measurement unit. Further, since the converter 14 has the same configuration as that of the converter 14 illustrated in FIG. 1, the description thereof will not be repeated.

The pipe unit 312 includes a sampling pipe 320 and the flowmeter 322. The sampling pipe 320 is a pipe which is connected to the measurement subject pipe and collects a part of the circulating gas flowing inside the measurement subject pipe, where one end portion is disposed inside the measurement subject pipe and the other end portion is connected to the downstream pipe (the exhaust pipe). Further, the flowmeter 322 which measures the flow rate of the circulating gas flowing inside the sampling pipe 320 is disposed on the path of the sampling pipe 320. Further, the converter 14 is disposed inside the pipe line of the sampling pipe 320. Further, in a region where the converter 14 is disposed in the sampling pipe 320, the diameter of the pipe line is larger than those of the other regions. That is, the pipe unit of the embodiment is formed as one pipe.

The measurement device 316 includes an upstream side measurement unit 330, a downstream side measurement unit 332, and a measurement device body 334. The upstream side measurement unit 330 is disposed at the upstream side in relation to the arrangement position of the converter 14 of the sampling pipe 320, and measures the concentration of the ammonia of the circulating gas (the circulating gas which is not subjected to the conversion of the ammonia compound, the second circulating gas) which flows inside the sampling pipe 320 and does not pass through the converter 14 yet. Further, the upstream side measurement unit 330 measures the concentration of the gas by causing the laser beam as the measurement light to be incident into the sampling pipe 320 and receiving the laser beam passing through the sampling pipe 320.

The upstream side measurement unit 330 includes an input pipe 342a, an output pipe 344a, windows 346a and 348a, an optical fiber 350a, a light incident portion 352a, and a light receiving portion 354a.

The input pipe 342a is a pipe-like member, and one end portion is connected to the sampling pipe 320. Further, the connection portion of the sampling pipe 320 with respect to the input pipe 342a is substantially opened in the same shape as that of the opening of the input pipe 342a (the opening of the end portion). That is, the input pipe 342a is connected to the sampling pipe 320 in a state where air may be circulated. Further, the other end portion of the input pipe 342a is provided with the window 346a, and is sealed by the window 346a. Further, the window 346a is formed by a light transmitting member, for example, a transparent glass, a resin, and the like. Accordingly, in the input pipe 342a, the end portion provided with the window 346a may permit the transmission of the light while the air is not circulated.

As illustrated in FIG. 6, the input pipe 342a is formed in a circular cylindrical shape in which the area of the opening (that is, the opening blocked by the window 346a) near the window 346a is substantially identical to the area of the end portion (that is, the opening connected to the sampling pipe 320) near the sampling pipe 320. Further, the shape of the input pipe 342a is not limited to the circular cylindrical shape, and a cylindrical shape which permits the transmission of the air and the light may be used. That is, various shapes may be adopted. For example, the cross-section may be formed in a shape of a square, a polygon, an ellipse, and an asymmetrical curved surface. Further, a shape may be adopted in which a shape and a diameter of a cylindrical cross-section change depending on the position.

The output pipe 344a is a pipe-like member which has substantially the same shape as that of the input pipe 342a, where one end portion is connected to the sampling pipe 320 and the other end portion of the output pipe 344a is provided with the window 348a. In a state where the air may be also circulated between the output pipe 344a and the sampling pipe 320, the end portion provided with the window 348a may not permit the circulation of the air and may permit the transmission of the light. Further, the output pipe 344*a* is disposed so that the axis is substantially identical to the axis of the input pipe 342*a*. That is, the input pipe 342*a* and the output pipe 344*a* are disposed at the facing positions in the sampling pipe 320.

Further, the output pipe 344*a* is also formed in a circular cylindrical shape in which the area of the opening (that is, the opening blocked by the window 348*a*) of the end portion near the window 348*a* is substantially identical to the area of the end portion (that is, the opening of the portion connected to the sampling pipe 320) near the sampling pipe 320. Further, the shape of the output pipe 344*a* is also not limited to the circular cylindrical shape, and a cylindrical shape which permits the transmission of the air and the light may be used. That is, various shapes may be adopted. For example, the cross-section may be formed in a shape of a square, a polygon, an ellipse, and an asymmetrical curved surface. Further, a shape may be adopted in which a shape and a diameter of a cylindrical cross-section change depending on the position.

Next, the optical fiber 350*a* guides the laser beam output from the measurement device body 334 to the light incident portion 352*a*. That is, the laser beam output from the measurement device body 334 is incident to the light incident portion 352*a*. The light incident portion 352*a* is an optical system (a mirror, a lens, and the like) disposed in the window 346*a*, and the laser beam guided by the optical fiber 350*a* is incident from the window 346*a* into the input pipe 342*a*. The laser beam which is incident to the input pipe 342*a* passes through the sampling pipe 320 from the input pipe 342*a*, and reaches the output pipe 344*a*.

The light receiving portion 354*a* is a light receiving portion which receives the laser beam passing inside the sampling pipe 320 and output from the window 348*a*. The light receiving portion 354*a* transmits the intensity of the received laser beam as the light receiving signal to the measurement device body 334.

In the upstream side measurement unit 330, the laser beam which is supplied from the measurement device body 334 to the optical fiber 350*a* passes through the light incident portion 352*a*, the window 346*a*, the input pipe 342*a*, the sampling pipe 320, the output pipe 344*a*, and the window 348*a*, and is incident to the light receiving portion 354*a*. Accordingly, the upstream side measurement unit 330 may detect the output of the laser beam which passes through a region where the circulating gas (the second circulating gas) which does not pass through the converter 14 yet flows. Accordingly, the upstream side measurement unit 330 may measure the second measurement value as in the upstream side measurement unit 230.

The downstream side measurement unit 332 is installed at the downstream side in relation to the arrangement position of the converter 14 of the sampling pipe 320, and measures the concentration of the ammonia of the circulating gas (the circulating gas which is subjected to the conversion of the ammonia compound, the first circulating gas) which flows inside the sampling pipe 320 and passes through the converter 14. Further, the downstream side measurement unit 332 also measures the concentration of the gas by causing the laser beam as the measurement light to be incident into the sampling pipe 320 and receiving the laser beam passing through the sampling pipe 320. The downstream side measurement unit 332 includes an input pipe 342*b*, an output pipe 344*b*, windows 346*b* and 348*b*, an optical fiber 350*b*, a light incident portion 352*b*, and a light receiving portion 354*b*. Further, since the downstream side measurement unit 332 basically has the same configuration as that of the upstream side measurement unit 330 except for the arrangement position of the measurement unit, the description thereof will not be repeated.

In the downstream side measurement unit 332, the laser beam which is supplied from the measurement device body 334 to the optical fiber 350*b* passes through the light incident portion 352*b*, the window 346*b*, the input pipe 342*b*, the sampling pipe 320, the output pipe 344*b*, and the window 348*b*, and is incident to the light receiving portion 354*b*. Accordingly, the downstream side measurement unit 332 may detect the output of the laser beam which passes through a region where the circulating gas (the first circulating gas) passing through the converter 14 flows. Accordingly, the downstream side measurement unit 332 may measure the first measurement value as in the downstream side measurement unit 232.

The measurement device body 334 basically has the same configuration as that of the measurement device body 44 except that the laser beam is output to two measurement units, the upstream side measurement unit 330 and the downstream side measurement unit 332 and the light receiving signals are received from two measurement units. That is, the measurement device body has the same configuration as that of the measurement device body 234.

The measurement device body 334 measures the concentration of the ammonia contained in the first circulating gas based on the intensity of the laser beam output to the downstream side measurement unit 332 and the light receiving signal transmitted from the downstream side measurement unit 332 and measures the concentration of the ammonia contained in the second circulating gas based on the intensity of the laser beam output to the upstream side measurement unit 330 and the light receiving signal transmitted from the upstream side measurement unit 330. The measurement device body 334 transmits the measurement result to the controller 318.

Further, the flowmeter 322 is disposed between the upstream side measurement unit 330 and the converter 14 on the path of the sampling pipe 320, and measures the flow rate of the circulating gas (the second circulating gas) which does not pass through the converter 14 yet. Further, the flowmeter 324 is disposed at the downstream side in relation to the downstream side measurement unit 332 on the path of the sampling pipe 320, and measures the flow rate of the circulating gas (the first circulating gas) which passes through the converter 14. The flowmeter 322 and the flowmeter 324 transmit the measurement results of the flow rates to the controller 318.

The controller 318 controls the operations of the respective units of the pipe unit 312, the converter 14, the measurement device 316, and the flowmeters 322 and 324 as in the controller 18. Further, the controller 318 measures (calculates) the concentration of the ammonia compound contained in the circulating gas (the concentration of the ammonia compound of the circulating gas) based on the measurement result transmitted from the measurement device 316. Further, the calculation method is the same as the calculation method of the controller 18.

With the above-described configuration, the ammonia compound concentration measuring device 300 may measure the concentration of the ammonia compound of the measurement subject contained in the circulating gas even when the measurement units are respectively provided at the upstream side and the downstream side of the region where the converter 14 (the thermal decomposition layer 39) is disposed. Further, as in the ammonia compound concentration measuring device 10, a so-called TDLAS-type measurement device is used as the measurement device and the concentration of the ammonia in the circulating gas is measured by the measurement device, thereby obtaining the same effect as described above. Further, the ammonia compound concentration measuring device 300 may also correct the calculation value of the concentration of the ammonia compound contained in the circulating gas based on the measurement results of the flowmeters 322 and 324, and hence may perform the calculation with the higher precision.

Further, the ammonia compound concentration measuring device 300 may also separately measure the first circulating gas and the second circulating gas without separating the pipe for guiding the circulating gas into two pipes by respectively installing two measurement units, the measurement units 330 and 332 at the upstream side and the downstream side of the region where the thermal decomposition layer 39 is disposed. Further, even in this case, it is possible to measure the concentration of the ammonia contained in the first circulating gas and the concentration of the ammonia contained in the second circulating gas at the same time. Accordingly, there is no need to change the passageway, and hence it is possible to further continuously measure the concentration of the ammonia compound of the measurement subject contained in the circulating gas. Further, since the measurement may be performed without changing the passageway, the responsiveness of the measurement may be also further improved. Further, the gas of the measurement subject may be set as the same circulating gas. That is, the circulating gas measured by the upstream side measurement unit 330 may be converted, and then may be measured by the downstream side measurement unit 332.

Further, the ammonia compound concentration measuring device 300 may directly measure the circulating gas flowing inside the sampling pipe 320. Accordingly, the ammonia compound concentration measuring device may be installed just by forming an opening in the sampling pipe 320 without providing the measurement cell. Further, in the above-described embodiment, a case has been described in which the sampling pipe 320 is provided, but the invention is not limited thereto. That is, the sampling pipe may be directly installed in the measurement subject pipe. Even in a case where the sampling pipe is directly provided in the measurement subject pipe, there is no need to provide an exclusive measurement cell. Accordingly, it is possible to perform the measurement without changing the flow rate and the flow speed of the circulating gas flowing inside the measurement subject pipe.

Further, in the above-described embodiment, the input pipe and the output pipe are coaxially provided, but the invention is not limited thereto. For example, a configuration may be adopted in which an optical mirror is provided inside the sampling pipe and the laser beam incident from the window of the input pipe is reflected as multiple laser beams by the optical mirror inside the measurement cell so that the laser beams reach the window of the output pipe. When the laser beam is reflected as multiple laser beams in this way, the laser beams may pass through the larger region inside the sampling pipe. Accordingly, it is possible to reduce an influence of the distribution of the concentration of the circulating gas flowing inside the sampling pipe (a variation in the flow rate or the density of the circulating gas and a variation in the distribution of the concentration inside the circulating gas), and hence to accurately detect the concentration.

Further, in the above-described embodiment, the input pipe and the output pipe are directly provided in the sampling pipe, but a configuration may be adopted in which the input pipe and the output pipe are installed in a pipe having the same diameter as that of the sampling pipe and the pipe is fitted into a part of the sampling pipe. That is, a part of the sampling pipe may be cut out, and the pipe provided with the input pipe and the output pipe may be fitted into the cut portion.

Fifth Embodiment

Figure 7:
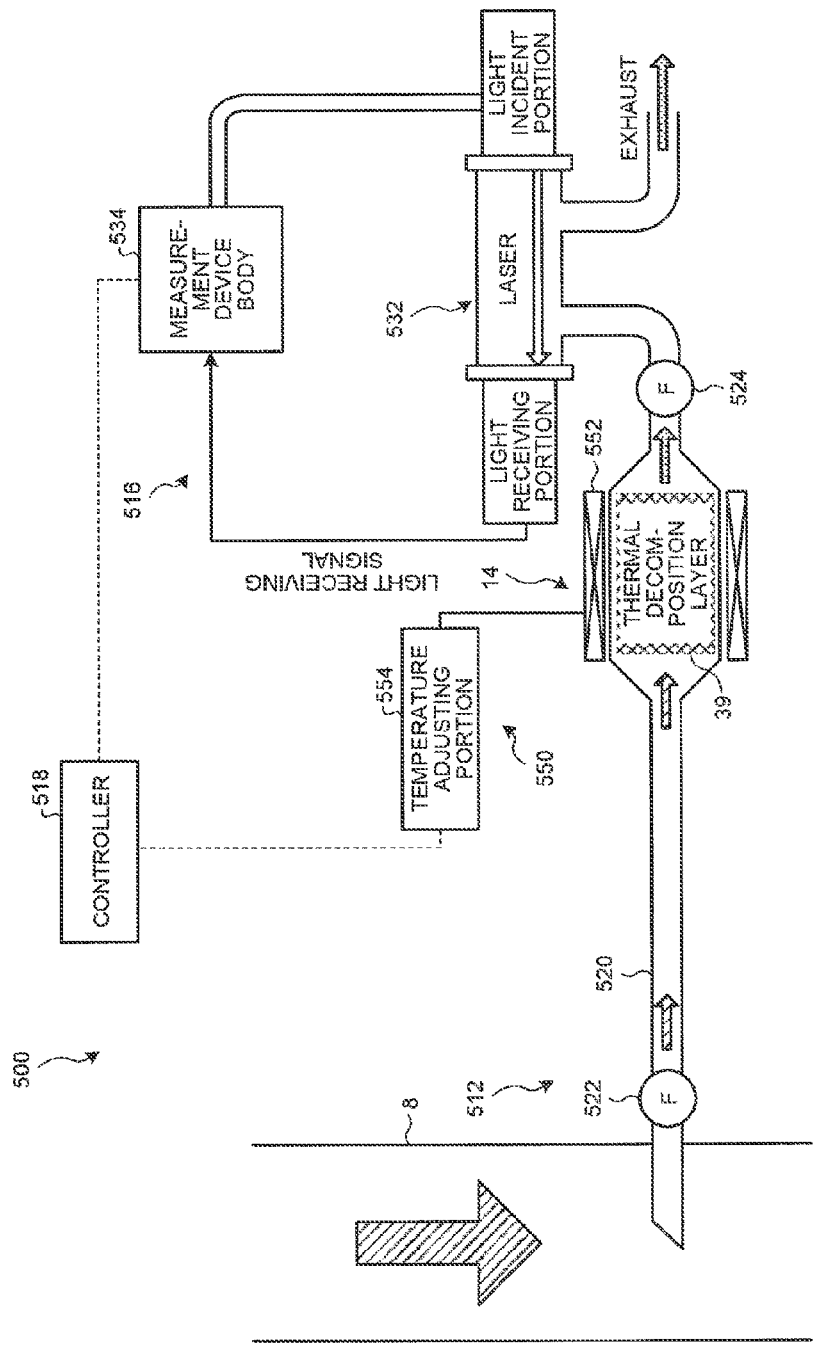
FIG. 7 is a schematic diagram illustrating a schematic configuration of another embodiment of the ammonia compound concentration measuring device.

FIG. 7 is a schematic diagram illustrating a schematic configuration of another embodiment of the ammonia compound concentration measuring device. An ammonia compound concentration measuring device 500 illustrated in FIG. 7 includes a pipe unit 512, the converter 14, a measurement device 516, a controller 518, flowmeters 522 and 524, and a switching unit 550.

The pipe unit 512 includes a sampling pipe 520. The sampling pipe 520 is a pipe which is connected to the measurement subject pipe 8 and collects a part of the circulating gas flowing inside the measurement subject pipe 8, where one end portion is disposed inside the measurement subject pipe 8 and the other end portion is connected to a measurement unit 532 of the measurement device 516. Further, the converter 14 is disposed inside the pipe line of the sampling pipe 520. Further, in a region where the converter 14 is disposed in the sampling pipe 520, the diameter of the pipe line is larger than those of the other regions. That is, the pipe unit of the embodiment is formed as one pipe.

The measurement device 516 includes the measurement unit 532 and a measurement device body 534. In the measurement unit 532, the upstream side end portion is connected to one end portion (the downstream side end portion) of the sampling pipe 520 and the downstream side end portion is connected to the farther downstream side pipe (the exhaust pipe or the like). The circulating gas which passes through the converter 14 is supplied to the measurement unit 532.

The measurement device body 534 outputs the laser beam to the measurement unit 532 and receives the light receiving signal from the measurement unit 532 so as to measure the concentration of the ammonia. The measurement device body basically has the same configuration as that of the measurement device body 44.

The switching unit 550 is disposed so as to be connected to the converter 14. The switching unit 550 is a unit which selects a state where the converter 14 thermally decomposes the ammonia compound or a state where the converter 14 does not thermally decompose the ammonia compound, and includes a heating mechanism 552 and a temperature adjusting portion 554. The heating mechanism 552 is a mechanism which heats the thermal decomposition layer 39 of the converter 14, and various heating mechanisms may be used. Further, the heating mechanism 552 may use the temperature adjusting mechanism constituting the thermal decomposition layer 39 of the converter 14. That is, a temperature adjusting mechanism (an image furnace or the like) of the converter 14 may be used as the heating mechanism 552.

The temperature adjusting portion 554 controls the heating operation of the heating mechanism 552 so as to adjust the temperature of the thermal decomposition layer 39. For example, the temperature adjusting portion 554 controls whether to perform the heating of the heating mechanism 552, so that the circulating gas passing through the thermal decomposition layer 39 becomes about 100° C. or about 300° C. Further, the converter 14 of the embodiment is a mechanism which adjusts the temperature of the thermal decomposition layer 39 by the switching unit 550.

The controller 518 controls the operations of the respective constituents of the pipe unit 512, the converter 14, the measurement device 516, and the flowmeters 522 and 524 as in the controller 18. Further, the controller 518 controls the heating mechanism 552 by the temperature adjusting portion 554 of the switching unit 550, thereby selecting a first state where the circulating gas passing through the converter 14 is heated to 300° C. or more or a second state where the circulating gas passing through the converter 14 is heated to about 100° C. Further, in the embodiment, the heating mechanism 552 does not heat the thermal decomposition layer 39 so that the circulating gas is maintained at about 100° C. and passes through the thermal decomposition layer 39.

Figure 8A:
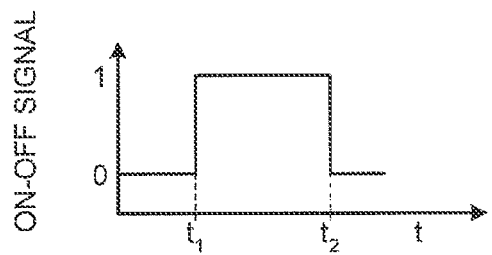
FIG. 8A is a diagram illustrating an operation of the ammonia compound concentration measuring device.
Figure 8B:
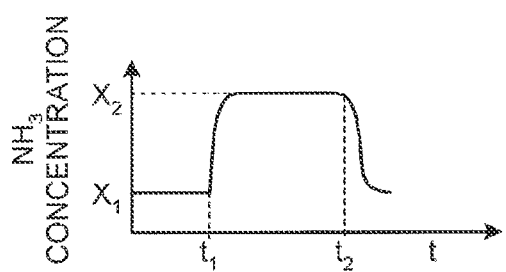
FIG. 8B is a diagram illustrating an operation of the ammonia compound concentration measuring device.

Hereinafter, this will be described in detail by using FIGS. 8A and 8B. Here, FIGS. 8A and 8B are diagrams illustrating an operation of the ammonia compound concentration measuring device. Further, the horizontal axis indicates the time t in FIGS. 8A and 8B, the vertical axis indicates the ON-OFF signal in FIG. 8A, and the vertical axis indicates the concentration of the ammonia in FIG. 8B. Further, in FIG. 8A, the ON signal is set to 1 and the OFF signal is set to 0. Here, when the ON signal is output, the switching unit 550 switches the converter 14 to the first state. When the OFF signal is output, the switching unit 550 switches the converter 14 to the second state. Further, the concentration of the ammonia ($NH_3$) of FIG. 8B is the concentration of the ammonia at the downstream side of the converter 14.

For example, as illustrated in FIG. 8A, the controller 518 outputs the OFF signal so that the heating mechanism 552 does not heat the thermal decomposition layer 39, outputs the ON signal at time $t_1$ so that the heating mechanism 552 heats the thermal decomposition layer 39, and outputs the OFF signal again at time $t_2$ after a predetermined time so that the heating mechanism 552 does not heat the thermal decomposition layer 39. Accordingly, the converter 14 becomes the second state before the time $t_1$, the converter 14 becomes the first state from the time $t_1$ to the time $t_2$, and the converter 14 becomes the second state again after the time $t_2$.

In accordance with this state, the converter 14 becomes a state where the ammonia compound directly passes therethrough before the time $t_1$, becomes a state where the ammonia compound is thermally decomposed into the ammonia from the time $t_1$ to the time $t_2$, and again becomes a state where the ammonia compound directly passes therethrough after the time $t_2$. Accordingly, only the ammonia basically contained in the circulating gas before the conversion (the coexistent gas, the ammonia which is contained in the circulating gas from the collection time) is contained in the circulating gas passing through the converter 14 before the time $t_1$ and after the time $t_2$. Then, the ammonia produced by thermally decomposing the ammonia compound using the converter 14 is contained in the circulating gas in addition to the coexistent gas from the time $t_1$ to the time $t_2$. Accordingly, as illustrated in FIG. 8B, the concentration of the ammonia is low before the time $t_1$ (a concentration $X_1$), the concentration of the ammonia is high from the time $t_1$ to the time $t_2$ (a concentration $X_2$), and the concentration of the ammonia is low again after the time $t_2$ (the concentration $X_1$).

By using the relation of FIG. 8B, the controller 518 measures the concentration of the ammonia of the circulating gas (the circulating gas which is not subjected to the conversion of the ammonia compound, the second circulating gas) which passes through the converter 14 before the time $t_1$ and after the time $t_2$ and is supplied to the measurement unit, and measures the concentration of the ammonia of the circulating gas (the circulating gas which is subjected to the conversion of the ammonia compound, the first circulating gas) which passes through the converter 14 from the time $t_1$ to the time $t_2$ and is supplied to the measurement unit. Accordingly, the controller calculates the concentration of the ammonia derived from the ammonia compound contained in the circulating gas and further measures (calculates) the concentration of the ammonia compound of the measurement subject contained in the circulating gas from the result.

With the above-described configuration, the ammonia compound concentration measuring device 500 may measure the concentration of the ammonia compound of the measurement subject contained in the circulating gas by repeating the ON/OFF (execution/stop) of the conversion (thermal decomposition) of the ammonia compound through the adjustment of the heating state (ON/OFF) of the circulating gas using the converter 14 by the switching unit 550. Even in this case, as in the ammonia compound concentration measuring device 10, a so-called TDLAS-type measurement device is used as the measurement device and the ammonia obtained by converting the ammonia compound of the measurement subject is set as the measurement subject, thereby obtaining the same effect as described above.

Further, in the embodiment, since it takes time for the conversion, the measurement is intermittently performed as in the ammonia compound concentration measuring device 10, but the concentration may be measured by one measurement unit.

Sixth Embodiment

Figure 9:
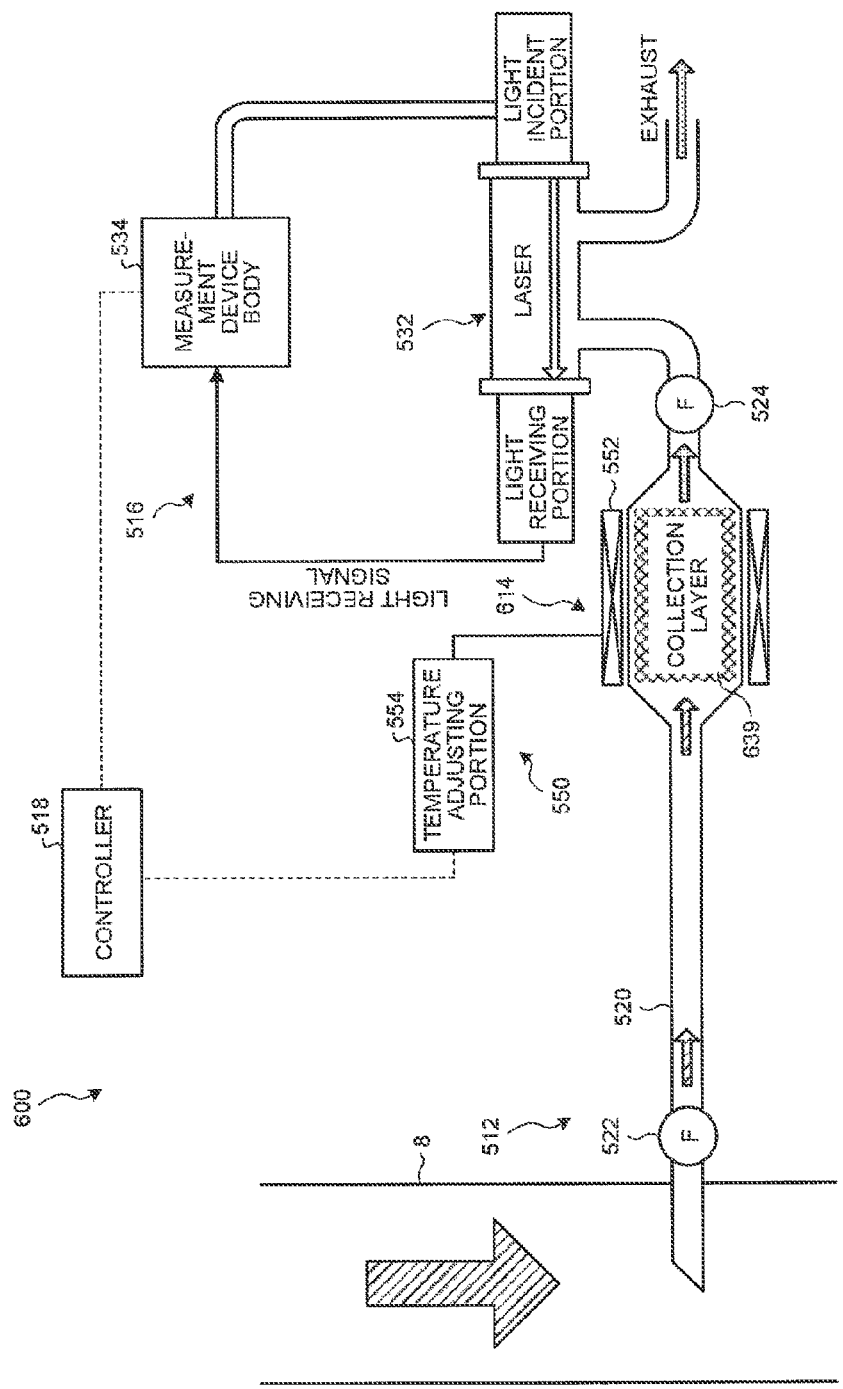
FIG. 9 is a schematic diagram illustrating a schematic configuration of another embodiment of the ammonia compound concentration measuring device.

FIG. 9 is a schematic diagram illustrating a schematic configuration of another embodiment of the ammonia compound concentration measuring device. An ammonia compound concentration measuring device 600 illustrated in FIG. 9 includes the pipe unit 512, a converter 614, the measurement device 516, the controller 518, the flowmeters 522 and 524, and the switching unit 550. Further, the ammonia compound concentration measuring device 600 illustrated in FIG. 9 is the same as the ammonia compound concentration measuring device 500 illustrated in FIG. 7 except for the configuration of the converter 614. Therefore, hereinafter, the specific point of the ammonia compound concentration measuring device 600 will be described.

The converter 614 includes a collection layer 639. The collection layer 639 is a material which absorbs the ammonia compound, and is disposed in a region where the ammonia compound is thermally decomposed, that is, a region where the thermal decomposition layer is disposed. As the collection layer 639, a porous material may be used. In particular, it is desirable to use a material which selectively absorbs the ammonia compound. The collection layer 639 absorbs the ammonia compound contained in the circulating gas passing therethrough. Thus, the circulating gas which passes through the collection layer 639 becomes a state where the ammonia compound is reduced or removed.

Further, a mechanism which heats the circulating gas of the converter 614 becomes the heating mechanism 552 of the switching unit 550. That is, the converter 614 thermally decomposes the ammonia compound absorbed to the collection layer 639 into the ammonia by heating a region where the collection layer 639 is disposed using the heating mechanism 552.

In this way, the ammonia compound concentration measuring device 600 provides the collection layer 639 which absorbs the ammonia compound as the converter 614. Accordingly, when the ammonia compound is thermally decomposed into the ammonia through the converter 614 by the switching unit 550, the absorbed ammonia compound is also thermally decomposed into the ammonia in addition to the ammonia compound contained in the passing circulating gas.

Further, as in the embodiment, when collecting the ammonia compound, the concentration of the coexistent gas is measured based on the circulating gas of the second state, and further the calculation is performed based on the relation between the concentration of the ammonia detected during the conversion process and the time of absorbing the ammonia compound before the conversion process (for example, the concentration is averaged by the sum of the absorption time and the reaction time). Then, the concentration of the ammonia derived from the ammonia compound contained in the circulating gas is calculated, and the concentration of the ammonia compound of the measurement subject contained in the circulating gas is further measured (calculated) from the result.

With the above-described configuration, the ammonia compound concentration measuring device 600 may measure the concentration of the ammonia compound of the measurement subject contained in the circulating gas by repeating the absorption and the thermal decomposition of the ammonia compound using the collection layer 639 which absorbs the ammonia compound to the thermally decomposed region. Even in this case, as in the ammonia compound concentration measuring device 10, a so-called TDLAS-type measurement device is used as the measurement device and the ammonia obtained by converting the ammonia compound of the measurement subject is set as the measurement subject, thereby obtaining the same effect as described above.

Further, since it is possible to decompose the more ammonia compound into the ammonia during the thermal decomposition by collecting the ammonia compound using the collection layer 639, it is possible to further appropriately detect a change in the concentration of the ammonia caused by the ammonia compound even when the amount of the ammonia compound contained in the circulating gas is small. Further, since the ammonia compound is collected by the collection layer 639, it is possible to thermally decompose the ammonia compound contained in the circulating gas into the ammonia at the higher percentage. Accordingly, the measurement precision may be further improved.

Further, in the embodiment, since it takes time for the conversion, the measurement is intermittently performed as in the ammonia compound concentration measuring device 10, but the concentration may be measured by one measurement unit.

Here, the invention is not limited to the above-described embodiments, and various embodiments may be adopted. For example, the respective embodiments may be combined with each other. For example, the collection layer may be added to the first to fourth embodiments. In this way, when the thermal decomposition layer is provided with the collection layer, the ammonia compound may be thermally decomposed into the ammonia at the higher percentage. Accordingly, the measurement precision may be further improved.

Further, the first to fourth embodiments may be provided with the temperature adjusting mechanism (the temperature adjusting portion, for example, the heating mechanism) which adjusts the temperature of the converter (the thermal decomposition region). In this way, when the temperature adjusting mechanism is provided, the temperature of the region (the atmosphere) for thermally decomposing the ammonia compound may be adjusted to the further appropriate range. Accordingly, the ammonia compound may be further appropriately thermally decomposed into the ammonia. Accordingly, the measurement precision may be further improved. Further, in all the above-described embodiments, the thermal decomposition layer of the converter or the heating mechanism as the temperature adjusting mechanism have been exemplified, but a cooling mechanism may be provided.

Further, in the ammonia compound concentration measuring device, a filter (a dust removing device) may be installed in the vicinity of the upstream side end portion of the sampling pipe when a large amount of soot dust is contained in the circulating gas. By providing the filter, the soot dust contained in the circulating gas may be removed. Further, even when the filter is provided, the ammonia compound concentration measuring device may use a simple filter compared to the case where the other measurement method is used since the allowance for the soot dust is large. Accordingly, it is possible to reduce a time delay caused by the arrangement of the filter, and hence to maintain the high responsiveness.

Further, the measurement unit may be provided with a purging gas supply portion which sprays air to the window of the measurement cell in a direction away from the window. By spraying the purging gas, it is possible to prevent a problem in which foreign matter adheres to the window and an error occurs in the measurement using the laser beam.

INDUSTRIAL APPLICABILITY

As described above, the ammonia compound concentration measuring device and the ammonia compound concentration measuring method according to the invention are useful to measure the ammonia compound contained in the circulating gas flowing inside the pipe line.

REFERENCE SIGNS LIST

8 measurement subject pipe
10, 100, 200, 300, 500, 600 ammonia compound concentration measuring device
12 pipe unit
14 converter
16 measurement device
18 controller
20 sampling pipe (inflow pipe)
22 first pipe
24 second pipe
26, 28 branch pipe
30 three-way valve
31 pump
32, 34 opening and closing valve
36, 38 flowmeter
39 thermal decomposition layer
42 measurement unit
44 measurement device body
45 measurement cell
46 optical fiber
48 light incident portion
50 light receiving portion
52 main pipe
54 inflow pipe
56 discharge pipe
58, 59 window
62 light emitting portion
64 light source driver
66 calculation portion

The invention claimed is:
1. An ammonia compound concentration measuring device which measures an ammonia compound concentration of a measurement subject contained in a circulating gas, the ammonia compound concentration measuring device comprising:

a pipe unit through which the circulating gas flows;

a converter which is disposed in the pipe unit and converts an ammonia compound contained in the circulating gas passing through the converter into ammonia;

a measurement device which measures a first measurement value as a concentration of ammonia contained in a first circulating gas flowing inside a pipe line with the converter out of the circulating gas flowing inside the pipe unit, and measures a second measurement value as a concentration of ammonia contained in a second circulating gas flowing inside a pipe line without the converter out of the circulating gas flowing inside the pipe unit;

a first flowmeter which is disposed at an upstream side in relation to the converter and measures a flow rate of the circulating gas flowing into the converter; and a second flowmeter which is disposed at a downstream side in relation to the converter and measures a flow rate of the circulating gas discharged from the converter; and a controller which controls operations of the pipe unit and the measurement device, and calculates the concentration of the ammonia compound contained in the circulating gas from a difference between the first measurement value and the second measurement value, wherein the measurement device includes a light emitting portion which outputs a laser beam having a wavelength absorbed by the ammonia and being in a near-infrared wavelength band, at least one measurement unit which includes a gas measurement cell causing the circulating gas to flow therethrough, an optical system causing the laser beam to be incident to the gas measurement cell, and a light receiving portion receiving the laser beam incident from the light emitting portion and passing through the gas measurement cell, a calculation portion which calculates the measurement value of the ammonia of the circulating gas flowing through the gas measurement cell based on an intensity of the laser beam output from the light emitting portion and an intensity of the laser beam received by the light receiving portion, and wherein the controller corrects and calculates a measurement value of the ammonia of the circulating gas based on a measurement result of the first flowmeter and a measurement result of the second flowmeter.

2. The ammonia compound concentration measuring device according to claim 1, wherein the pipe unit includes an inflow pipe into which the circulating gas flows, a first pipe which is connected to a downstream side end portion of the inflow pipe in a circulating gas flow direction and is provided with the converter, a second pipe which is connected to the downstream side end portion of the inflow pipe in the circulating gas flow direction together with the first pipe and is not provided with the converter, and a three-way valve which is connected to a downstream side end portion of the first pipe, a downstream side end portion of the second pipe, and an upstream side end portion of the gas measurement cell in the circulating gas flow direction, wherein the controller connects the downstream side end portion of the first pipe to the upstream side end portion of the gas measurement cell in the circulating gas flow direction by the three-way valve so as to cause the first circulating gas to flow into the measurement device and measures the first measurement value, and wherein the controller connects the downstream side end portion of the second pipe to the upstream side end portion of the gas measurement cell in the circulating gas flow direction by the three-way valve so as to cause the second circulating gas to flow into the measurement device, and measures the second measurement value.

3. The ammonia compound concentration measuring device according to claim 1, wherein the pipe unit includes an inflow pipe into which the circulating gas flows, a first pipe which is connected to a downstream side end portion of the inflow pipe in a circulating gas flow direction and is provided with the converter, and a second pipe which is connected to the downstream side end portion of the inflow pipe in the circulating gas flow direction together with the first pipe and is not provided with the converter, wherein the measurement device includes two measurement units, one measurement unit is disposed at a downstream side in relation to the converter in the circulating gas flow direction of the first pipe, and the other measurement unit is disposed in the second pipe.

4. The ammonia compound concentration measuring device according to claim 1, wherein the pipe unit includes an inflow pipe into which the circulating gas flows, and a retention pipe which is connected to a downstream side end portion of the inflow pipe in a circulating gas flow direction and is provided with the converter, wherein the measurement device includes two measurement units, one measurement unit is disposed at a downstream side in relation to the converter in the circulating gas flow direction of the retention pipe, and the other measurement unit is disposed at an upstream side in relation to the converter in the circulating gas flow direction of the retention pipe.

5. The ammonia compound concentration measuring device according to claim 1, wherein the converter is a thermal decomposition layer which thermally decomposes an ammonia compound into ammonia.

6. The ammonia compound concentration measuring device according to claim 5, wherein the converter includes a temperature adjusting portion which adjusts a temperature of the thermal decomposition layer.

7. The ammonia compound concentration measuring device according to claim 1, further comprising:

a switching unit which selects an execution or a stop of a conversion operation of the converter, wherein the pipe unit includes an inflow pipe into which the circulating gas flows, and a retention pipe which is connected to a downstream side end portion of the inflow pipe in a circulating gas flow direction and is provided with the converter, wherein in the measurement device, the measurement unit is disposed at a downstream side in relation to the converter in the circulating gas flow direction of the retention pipe, wherein the converter is a thermal decomposition layer which thermally decomposes an ammonia compound into ammonia, wherein the switching unit is a temperature adjusting portion which adjusts a temperature of the thermal decomposition layer, and wherein the controller selects a state where the conversion operation of the converter is executed or a state where the conversion operation of the converter is stopped so as to select a state where the first circulating gas flows into the measurement unit or a state where the second circulating gas flows thereinto.

8. The ammonia compound concentration measuring device according to claim 7,
wherein the switching unit causes the temperature adjusting portion to heat the circulating gas up to a temperature at which the ammonia compound is decomposed so that the conversion operation of the converter is executed and to stop the heating of the circulating gas so that the conversion operation of the converter is stopped.

9. The ammonia compound concentration measuring device according to claim 1,
wherein the converter further includes a collection layer which collects the ammonia compound.

10. The ammonia compound concentration measuring device according to claim 1,
wherein in the measurement unit, a laser beam passes inside a pipe which retains the converter.

11. The ammonia compound concentration measuring device according to claim 1,
wherein an entire amount of the circulating gas discharged from a device of the measurement subject flows inside the pipe unit.

12. The ammonia compound concentration measuring device according to claim 1,
wherein the pipe unit collects a part of the circulating gas from a measurement subject pipe through which an entire amount of the circulating gas discharged from a device to be measured flows.

13. An ammonia compound concentration measuring method which measures an ammonia compound concentration of a circulating gas flowing inside a pipe, the ammonia compound concentration measuring method comprising:
a first measurement step of outputting a laser beam having a wavelength absorbed by ammonia and being in a near-infrared wavelength band to a first circulating gas passing through a region provided with a converter for converting an ammonia compound into ammonia in the circulating gas flowing inside the pipe, receiving the laser beam passing through a pipe line through which the first circulating gas flows, and measuring a concentration of the ammonia contained in the first circulating gas as a first measurement value based on an intensity of the output laser beam and an intensity of the laser beam received by a light receiving portion;
a second measurement step of outputting a laser beam having a wavelength absorbed by ammonia and being in a near-infrared wavelength band to a second circulating gas not passing through a region provided with a converter for converting an ammonia compound into ammonia in the circulating gas flowing inside the pipe, receiving the laser beam passing through a pipe line through which the second circulating gas flows, and measuring a concentration of the ammonia contained in the circulating gas as a second measurement value based on an intensity of the output laser beam and an intensity of the laser beam received by the light receiving portion;
a first flow measuring step of measuring a flow rate of the circulating gas flowing into the converter by using a first flowmeter which is disposed at an upstream side in relation to the converter;
a second flow measuring step of measuring a flow rate of the circulating gas discharged from the converter by using a second flowmeter which is disposed at a downstream side in relation to the converter,
a calculation step of calculating a measurement value of the concentration of the ammonia compound contained in the circulating gas from a difference between the first measurement value and the second measurement value, and
a correcting step of correcting the measurement value of the ammonia of the circulating gas based on a measurement result of the first flow measuring step and a measurement result of the second flow measuring step.

* * * * *